(12) United States Patent
MacNicol

(10) Patent No.: US 7,037,686 B2
(45) Date of Patent: May 2, 2006

(54) HUMAN CYTOPLASMIC POLYADENYLATION ELEMENT BINDING PROTEIN AND USES THEREOF

(76) Inventor: Angus M. MacNicol, 5428 Southwood Rd., Little Rock, AR (US) 72205

( * ) Notice: Subject to any disclaimer, the term of this patent is extended or adjusted under 35 U.S.C. 154(b) by 0 days.

(21) Appl. No.: 10/945,703

(22) Filed: Sep. 21, 2004

(65) Prior Publication Data
US 2005/0095632 A1 May 5, 2005

Related U.S. Application Data

(63) Continuation-in-part of application No. 10/349,852, filed on Jan. 23, 2003.

(60) Provisional application No. 60/351,121, filed on Jan. 23, 2002.

(51) Int. Cl.
C12P 21/02 (2006.01)
C12Q 1/68 (2006.01)
C12N 15/12 (2006.01)
C12N 5/08 (2006.01)
C12N 21/04 (2006.01)

(52) U.S. Cl. .......... 435/69.8; 435/6; 435/366; 435/320.1; 536/23.1; 536/24.3

(58) Field of Classification Search .......... 435/69.8, 435/6, 366, 320.1; 536/23.1, 24.3
See application file for complete search history.

(56) References Cited

OTHER PUBLICATIONS

Welk et al., "Identification and characterization of the gene encoding human cytoplasmic polyadenylation element binding protein," Genes 263: 113-120, published Jan. 24, 2001.*
NCBI GenBank record No. X65305, disclosure of the Promega pGEM®-4Z cloning vector, first submitted Mar. 23, 1992.*
Promega Technical Bulletin No. 036, pGEM®-4Z Vector (Feb. 2004).*
Sequence alignment, Result 1 from a search of SEQ ID NO: 1 in the GenEmbl database.*

* cited by examiner

*Primary Examiner*—Robert A. Wax
*Assistant Examiner*—Rosanne Kosson
(74) *Attorney, Agent, or Firm*—Benjamin Aaron Adler

(57) ABSTRACT

The present invention provides genomic and cDNA encoding human cytoplasmic polyadenylation element binding protein, expression vectors comprising human cytoplasmic polyadenylation element binding protein cDNA and host cells that contain the expression vectors. Also provided are recombinant human cytoplasmic polyadenylation element binding protein and polypeptides derived thereof. In addition, the present invention reports that the human Mos 3' untranslated region (3' UTR) contains a functional cytoplasmic polyadenylation element (CPE), interacts with the human CPEB1 protein and directs maturation-dependent cytoplasmic polyadenylation of the endogenous Mos mRNA.

5 Claims, 18 Drawing Sheets

```
                    CPE                  HEX
Hu Mos WT      ...TGTTTTTAAAG.....AGTTTTAGAAAATAAAGTT...(SEQ ID NO: 25)
Hu Mos mut 1   ...TGTTTTTAAAG.....AGTTTggGAAAATAAAGTT...(SEQ ID NO: 26)
Hu Mos mut 2   ...TGTTTgggAAG.....AGTTTTAGAAAATAAAGTT...(SEQ ID NO: 27)
Hu Mos mut 3   ...TGTTTgggAAG.....AGTTTggGAAAATAAAGTT...(SEQ ID NO: 28)
```

```
                                                             50
TA ATG TCAATA ATG TTTTCTGGCATTGCTACTTCAACATCGTCTTCC ATG T

*100
CTGGCACTGGTTTGGAGCACTCATCTCTATCAGATTGTCTTCTGCTAATT

150
CCTCTGGT ATG TTAACTCTTGGATTTCTCCAAGGTCC ATG TCTTGGAAAT

200
CTTCACTCCCAACCTTTTTTTGTCATATCTACAGTTTCTTTC ATG ATTTC

250
CTGTATTGGCTCTGTGGTAAATCTGTGAAGTC ATG TACAACATCTGGAAA

300
CAGTTTTTTTAAGCAGGAATTTATTATTTTGGGC ATGATG GCTTTC ATG G

▽        350
ATTTTTCTGTAACA ATG ATGGCATTGTCACTGGAAGAAGAAGCAGGAAGG
               M   A  L  S  L  E  E  E  A  G  R

400
ATAAAAGATTGCTGGGACAACCAGGAAGCACCTGCTCTCTCCACGTGTAG
 I  K  D  C  W  D  N  Q  E  A  P  A  L  S  T  C  S>

450
TAATGCCAATATCTTTCGAAGGATAAATGCCATATTGGATAATTCTCTGG
 N  A  N  I  F  R  R  I  N  A  I  L  D  N  S  L
```

Fig. 1A

```
                                                           500
ATTTCAGTAGAGTCTGCACTACACCTATAAACCGAGGAATTCATGATCAT
 D   F   S   R   V   C   T   T   P   I   N   R   G   I   H   D   H> hCPEB (short)         550
           ▼
TTGCCAGACTTCCAGGACTCTGAAGAAACAGTTACAAGCAGGATGCTTTT
 L   P   D   F   Q   D   S   E   E   T   V   T   S   R   M   L   F 600
CCCAACCTCTGCGCAAGAATCTTCCCGTGGCCTCCCAGATGCAAATGACT
   P   T   S   A   Q   E   S   S   R   G   L   P   D   A   N   D>

650
TGTGCCTTGGCCTGCAGTCCCTCAGTCTGACAGGCTGGGACCGACCCTGG
 L   C   L   G   L   Q   S   L   S   L   T   G   W   D   R   P   W

▽                 700
AGCACCCAGGACTCAGATTCCTCAGCCCAGAGCAGCACACACTCGGTACT
 S   T   Q   D   S   D   S   S   A   Q   S   S   T   H   S   V   L>

750
GAGCATGCTCCATAACCCACTGGGAAATGTCCTAGGAAAACCCCCTTGA
   S   M   L   M   N   P   L   G   N   V   L   G   K   P   P   L

800
GCTTCCTGCCTC TGGATCC CCTTGGGTCTGACTTGGTGGACAAGTTTCCA
   S   F   L   P   L   D   P   L   G   S   D   L   V   D   K   P   P>
```

Fig. 1B

```
                                                                 850
GCACCCTCAGTTAGAGGATCACGCCTGGACACCCGGCCCATCCTGGACTC
 A   P   S   V   R   G   S   R   L   D  (T)  R   P   I   L   D  (S)

900
TCGATCTAGCAGCCCCTCTGACTCAGACACCAGTGGCTTCAGCTCTGGAT
  R   S   S   S   P   S   D   S   D   T   S   G   F   S   S   G>

▽                                  950
CAGATCATCTCTCAGATTTGATTTCAAGCCTTCGCATTTCTCCACCTCTG
 S   D   H   L   S   D   L   I   S   S   L   R   I   S   P   P   L

1000
CCCTTCCTGTCTCTGTCAGGGGGTGGTCCCAGAGACCCTTTAAAGATGGG
  P   F   L   S   L   S   G   G   P   R   D   P   L   K   M   G>

1050
GGTAGGGTCTCGGATGGACCAAGAGCAAGCTGCTCTTGCTGCAGTCACTC
   V   G   S   R   M   D   Q   E   Q   A   A   L   A   A   V   T

1100
CCTCCCCAACCAGTGCTTCAAAGAGATGGCCAGGAGCTTCTGTGTGGCCA
  P   S   P   T   S   A   S   K   R   W   P   G   A   S   V   W>

1150
TCCTGGGACCTCCTCGAAGCTCCCAAAGACCCCTTCAGCATAGAGAGA
  S   W   D   L   L   E   A   P   K   D   P   F   S   I   E   R   E
```

Fig. 1C

```
                              ▽                  1200
GGCCAGGCTGCACCGACAAGCTGCAGCTGTGAATGAAGCCACCTGTACCT
  A  R  L  H  R  Q  A  A  A  V  N  E  A  T  C  T>

RRM1 ↰     1250
GGAGTGGCCAGCTTCCTCCCCGGAACTATAAGAACCCCATCTACTCTTGC
  W  S  G  Q  L  P  P  R  N  Y  K  N  P  I  Y  S  C

▽               1300
AAGGTGTTTCTAGGAGGTGTTCCTTGGGATATTACAGAAGCTGGATTAGT
  K  V  F  L  G  G  V  P  W  D  I  T  E  A  G  L  V>

1350
TAACACCTTCCGTGTTTTTGGCTCTTTGAGTGTGGAGTGGCCTGGTAAGG
  N  T  F  R  V  F  G  S  L  S  V  E  W  P  G  K

▽  1400
ATGGCAAGCATCCCCGGTGTCCTCCCAAAGGTAATATGCCTAAAGGGTAT
  D  G  K  H  P  R  C  P  P  K  G  N  M  P  K  G  Y>

1450
GTGTATCTGGTCTTCGAACTAGAGAAGTCTGTCCGATCCTTGCTTCAGGC
  V  Y  L  V  F  E  L  E  K  S  V  R  S  L  L  Q  A

1500
TTGCTCTCATGACCCGCTGAGCCCAGATGGCCTGAGTGAATATTATTTCA
  C  S  H  D  P  L  S  P  D  G  L  S  E  Y  Y  F>
```

Fig. 1D

```
                  ↰                              ▽                    1550
          AGATGTCCAGCCGAAGGATGCGCTGCAAGGAGGTGCAGGTGATCCCCTGG
           K  M  S  S  R  R  M  R  C  K  E  V  Q  V  T  P  W

1600
          GTATTAGCCGACAGTAACTTTGTCCGGAGCCCATCTCAGAGGCTTGACCC
            V  L  A  D  S  N  F  V  R  S  P  S  Q  R  L  D  P>

↱ RRM2                                                    1650
          CAGCAGGACGGTGTTTGTCGGTGCTCTGCATGGAATGCTAAATGCTGAGG
             S  R  T  V  F  V  G  A  L  H  G  M  L  N  A  E

1700
          CCCTGGCAGCCATCTTGAACGACCTATTTGGTGGAGTGGTGTATGCCGGG
           A  L  A  A  I  L  N  D  L  F  G  G  V  V  Y  A  G>

▽                       1750
          ATTGACACAGATAAGCACAAGTATCCCATTGGTTCTGGTCGTGTGACTTT
           I  D  T  D  K  H  K  Y  P  I  G  S  G  R  V  T  F

1800
          CAATAACCAACGGAGTTACCTGAAAGCAGTCAGCGCTGCTTTTGTGGAGA
           N  N  Q  R  S  Y  L  K  A  V  S  A  A  F  V  E>

▽                ↰           1850
          TCAAAACCACCAAGTTCACAAAGAAGGTTCAGATTGACCCCTACCTAGAA
           I  K  T  T  K  F  T  K  K  V  Q  I  D  P  Y  L  E
```

Fig. 1E

```
                                                        Znf                                    1900
                              GATTCTCTGTGTCATATCTGCAGTTCTCAGCCTGGTCCTTTCTTCTGTCG
                                D   S   L   C   H   I   C   S   S   Q   P   G   P   F   F   C   R>

▽                                      1950
                              AGATCAGGTCTGCTTCAAATACTTCTGCCGGAGCTGCTGGCACTGGCGGC
                                D   Q   V   C   F   K   Y   F   C   R   S   C   W   H   W   R

2000
                              ACAGCATGGAGGGCCTGCGCCACCACAGCCCCCTGATGCGGAACCAGAAG
                                H   S   M   E   G   L   R   H   H   S   P   L   M   R   N   Q   K>

2050
                              AACCGAGATTCCAGCTAGAGGAGCTGGCCTTGCCCAGTGGCCTGTGGCGC
                                N   R   D   S   S   *>  (SEQ ID NO: 3)

2100
                              CCAAAGCTGGCAGGTCAGGCAAGCAGCCTGCACCACCCTGCCACTGGCGA

2150
                              CCAGGGAGCTGGCTTCCCAAGGACAAGGGAAAATTGTAGTCACCTTTGCA

2200
                              CTTGCTGAATCTGTCTTTGTTTCTGCACTAATTAATGCACATTGAGTTTT

2250
                              GTCAGGTTTTGTTTTCAGGGGGTGTACCAAGGGCAAGGACCCTCTGGCTT
```

Fig. 1F

```
                                                                    2300
ACCCTCCAAGCGACTCTGTAGTTTTCCCAGATTTTAGTTCCTCATTTTGC

2350
AGATGAAAAGCGGGAAAAAAAAAAAAAAAAAATTCCTGAAGGTATTGA

2400
CACGGATGCCTACACCTAGGTTTATTTATTAAAGCGCTTTTTTACATTC

2450
CTTGCAATACTGATGGTGATGATGCGCAGGTCTCATTGGTTTCATTCTTG

2500
CAGTTGCCATACAGTGCCTTTCCATTTATTTAACCCCCACCTGAACGGCA

2550
TAAACTGAGTGTTCAGCTGGTGTTTTTTACTGTAAACAATAAGGAGACTT

2600
TGCTCTTCATTTAAACCAAAATCATATTTCATATTTTACGCTCGAGGGTT

2650
TTTACCGGTTCCTTTTTACACTCCTTAAAACAGTTTTTAAGTCGTTTGGA

2700
AGAAAATATTTTTTCTTTCCTGGCAGCTTTTAACATTATAGCAAATTTGT

2750
GTCTGGGGGACTGCTGGTCACTGTTTCTCACAGTTGCAAATCAAGGCATT

TGCAACCAAAAAAAAAAAAAAAAAAAAATG (SEQ ID NO: 1)
```

Fig. 1G

```
                                                 *50
GGCAGCGGGAAGCATCAGCAGCCTGATCACATGCTGGCCCAGTCTGTAAT

*        100
GCAGACGGGATAGGGGTGTGTGTGTGAGGGGAGGGGGCCTGTATGGCAAC

150
TGCTCTTGCCCCAGCGTCCCCAAAAGTGCAGAGGCAGCGGCTGCAGCATC

▼
CAGCCAGCTTGGATGTCTGGCCT (SEQ ID NO: 16)
```

Fig. 1H

```
                            CPE    Hex
5'-------21nt-------  UUUUAU AAUAAA ----15nt----3;  wt UTR

5'-------21nt-------  UUUggU AAUAAA ----15nt----3'  mut UTR
```

HUMAN CYTOPLASMIC POLYADENYLATION ELEMENT BINDING PROTEIN AND USES THEREOF

CROSS-REFERENCE TO RELATED APPLICATION

This is a continue-in-part application of patent application U.S. Ser. No. 10/349,852, filed Jan. 23, 2003, which claims the benefit of priority of provisional patent application U.S. Ser. No. 60/351,121, filed Jan. 23, 2002, now abandoned.

FEDERAL FUNDING LEGEND

This invention was produced in part using funds obtained through grants HD035688 and HD038081 from the National Institutes of Health. Consequently, the federal government has certain rights in this invention.

BACKGROUND OF THE INVENTION

1. Field of the Invention

The present invention relates generally to the fields of molecular biology and gene cloning. More specifically, the present invention relates to the identification and characterization of the gene encoding human cytoplasmic polyadenylation element binding protein and uses thereof.

2. Description of the Related Art

During meiotic maturation of human oocytes gene transcription is repressed (Braude et al., 1988) and required proteins are translated from pre-existing, maternally derived mRNAs (Pal et al., 1994). In model systems (*Drosophila, Xenopus*, and the mouse), certain maternally derived mRNAs which encode key regulators of cell cycle progression and pattern formation are translationally silent in immature oocytes and become translationally activated following hormonal stimulation (Davidson, 1986; Wickens et al., 1996). This translational activation has been correlated with the cytoplasmic polyadenylation of the mRNAs, a process directed by two elements within the mRNA 3' untranslated region (UTR) (reviewed in Richter, 1999). The first element is the AAUAAA polyadenylation hexanucleotide and the second element is a uridine-rich sequence of general consensus UUUUUAU termed the cytoplasmic polyadenylation element (CPE). In addition to directing cytoplasmic polyadenylation and translational activation, these cytoplasmic polyadenylation element sequences have also been implicated in mediating translational repression in immature oocytes (de Moor and Richter, 1999; Barkoff et al., 2000; Tay et al., 2000) and during the early phases of hormonally stimulated oocyte maturation (Charlesworth et al., 2000). Cytoplasmic polyadenylation element-mediated mRNA translational control has also been suggested to occur in mammalian neuronal cells (Wu et al., 1998).

A cytoplasmic polyadenylation element binding protein, CPEB, has been cloned from a number of species (Hake and Richter, 1994; Gebauer and Richter, 1996; Bally-Cuif et al., 1998; Walker et al., 1999) and has been implicated in mediating both polyadenylation-dependent translational activation and cytoplasmic polyadenylation element-directed translational repression (Hake and Richter, 1994; Stebbins-Boaz et al., 1996; Stutz et al., 1998; Minshall et al., 1999; Stebbins-Boaz et al., 1999; Mendez et al., 2000). While it is not clear how the cytoplasmic polyadenylation element binding protein can exert these apparently opposite effects on mRNA translation, there is some evidence that the C-terminal domain is necessary for translational repression while the N-terminal domain may regulate translational activation. It has been reported that overexpression of an N-terminally truncated form of the *Xenopus* cytoplasmic polyadenylation element binding protein (lacking the first 139 amino acids) did not significantly affect translational repression but did block both cytoplasmic polyadenylation and translational induction (Mendez et al., 2000).

Given the key role of cytoplasmic polyadenylation in the control of mRNA translation in model organisms, it is of interest to determine if a similar process occurred in humans. However, human cytoplasmic polyadenylation element binding protein has not been identified. Thus, the prior art is deficient in identifying a human cytoplasmic polyadenylation element binding protein which is essential for the study of mRNA translation control in human. The present invention fulfills this long-standing need and desire in the art by cloning a human cytoplasmic polyadenylation element binding protein.

Despite a critical role in the control of human fertility, the mechanisms regulating human oocyte maturation are not well characterized. In model organisms, accumulation of critical cell cycle regulatory proteins during oocyte meiotic maturation depends upon the regulated translation of maternally derived mRNAs (Wickens, et al., 2000; Mendez and Richter, 2001). The maternal mRNA encoding the Mos proto-oncogene is subject to tight translational regulation in oocytes from a variety of vertebrate species. The Mos protein is a serine/threonine kinase which activates the MAP kinase cascade through direct phosphorylation of the MAP kinase activator MEK (aka MAP kinase kinase) (Posada et al. 1993; Shibuya et al., 1996). In the mouse, Mos protein is absent from immature oocytes and maturation-dependent cytoplasmic polyadenylation correlates with the translational activation of the maternal Mos mRNA (Gebauer, et al., 1994). While mouse meiotic cell cycle progression does not depend on Mos translation, Mos protein function is necessary for arrest of the mature oocyte at meiotic metaphase II (Araki et al., 1996; Colledge et al. 1994; Hashimoto et al. 1994; Hashimoto, 1996). In addition to a requirement for meiotic metaphase II arrest (Sagata et al., 1989; Daar et al., 1991), Mos function is also required earlier during maturation of oocytes from the frog, *Xenopus laevis*, to mediate entry into Meiosis II after completion of Meiosis I in oocytes (Gross et al., 2000; Dupre et al., 2002).

Meiotic cell cycle progression has been best characterized in *Xenopus*, where the cytoplasmic polyadenylation and translational activation of select maternal mRNAs occur in a strict temporal order (Dupre et al., 2002; Hochegger et al., 2001; Howard et al., 1999; Nakajo et al., 2000; Sheets et al., 1994; Sheets et al., 1995; Ferby et al., 1999; Sagata et al., 1988; Charlesworth et al., 2000; Ballantyne et al., 1997; de Moor et al., 1997). The ability to regulate addition of a poly[A] tail extension in the oocyte cytoplasm requires a polyadenylation nucleotide sequence (typically AAUAAA) as well as additional 3' UTR regulatory sequences, including cytoplasmic polyadenylation elements (CPE) (reviewed in Richter, 2000) and polyadenylation response elements (PRE) (Charlesworth et al., 2002; Charlesworth et al., 2004). CPE sequences have been shown to repress mRNA translation in immature oocytes and to direct temporally late cytoplasmic polyadenylation and translational activation in maturing oocytes. Both aspects of CPE function appear to require the CPE-binding protein (CPEB1) (Gebauer et al., 1994; Charlesworth et al., 2000; Fox et al., 1989; McGrew et al., 1989; McGrew et al., 1990; Paris and Richter, 1990; Sallès et al., 1992; Standart and Dale, 1993; Stebbins-Boaz et al., 1996; Stutz et al., 1998; de Moor and Richter, 1999;

Minshall et al., 1999; Barkoff et al., 2000; Tay et al., 2000). Recent studies have demonstrated that the induction of a temporally early class of *Xenopus* maternal mRNAs, including the Mos mRNA, is directed by PRE sequences in a CPE- and CPEB1-independent manner (Charlesworth et al., 2002; Charlesworth et al., 2004). By contrast, induction of CPE- and CPEB1-dependent mRNAs occurs temporally late during oocyte maturation (Charlesworth et al., 2002; Charlesworth et al., 2004). While consensus CPE sequences are present in the Mos mRNA 3' UTRs from a variety of vertebrate species, it remains to be determined if PRE sequences also contribute to the temporal regulation of Mos mRNA translational activation in higher vertebrates.

Previous studies employing inhibition of protein synthesis in general or targeted ablation of the endogenous Mos mRNA, have suggested a role for regulated Mos mRNA translational control during human oocyte maturation (Hashiba et al., 2001; Pal et al., 1994). However, while a human CPEB1 protein has been characterized and shown to be expressed in human oocytes, the prior art is deficient in determining if regulated cytoplasmic polyadenylation of the maternal Mos mRNA occurs during human oocyte maturation. This study fulfills this long-standing need and desire in the art by showing that the human Mos 3' UTR contains a functional CPE sequence, interacts with the human CPEB1 protein and directs maturation-dependent cytoplasmic polyadenylation of the endogenous Mos mRNA. Unlike the *Xenopus* Mos mRNA, there is no evidence for PRE-directed regulation of the human Mos mRNA. The results presented herein suggest fundamental differences in 3' UTR regulatory element composition reflecting the differential temporal requirements for Mos mRNA translation during *Xenopus* and mammalian oocyte maturation.

SUMMARY OF THE INVENTION

The present invention reports the cloning of a human cytoplasmic polyadenylation element binding protein (hCPEB) with sequence-specific RNA binding activity. The data disclosed herein demonstrate that alternative splicing generates human cytoplasmic polyadenylation element binding protein mRNAs that encode proteins with a conserved C-terminal RNA binding domain but with different N-terminal regulatory domains. The human cytoplasmic polyadenylation element binding protein mRNA is expressed in the brain and heart as well as in immature oocytes, consistent with the hypothesis that cytoplasmic polyadenylation may regulate the translation of human mRNAs in both oocytes and somatic cells. The present invention also reports that the human Mos 3' untranslated region (3' UTR) contains a functional cytoplasmic polyadenylation element (CPE), interacts with the human CPEB1 protein and directs maturation-dependent cytoplasmic polyadenylation of the endogenous Mos mRNA.

In one embodiment of the present invention, there is provided an isolated DNA encoding human cytoplasmic polyadenylation element binding protein, expression vectors that contain the claimed DNA, as well as host cells that contains the expression vectors. The present invention also encompasses an isolated DNA which is complementary to the DNA disclosed herein.

The present invention further provides a recombinant human cytoplasmic polyadenylation element binding protein and polypeptides derived thereof. The human cytoplasmic polyadenylation element binding protein has the amino acid sequence of SEQ ID No. 3 or 4, and the polypeptide has at least 10 amino acid residues.

In another aspect of the present invention, there is provided a method of screening for compound that increases or decreases the RNA binding activity of human cytoplasmic polyadenylation element binding protein (hCPEB). The method involves the steps of (a) contacting human cytoplasmic polyadenylation element binding protein with a probe comprising cytoplasmic polyadenylation element (CPE) sequence in the presence of the compound; and (b) determining the cytoplasmic polyadenylation element sequence-specific binding activity of the human cytoplasmic polyadenylation element binding protein, wherein an increase in binding activity indicates the compound increases RNA binding activity of human cytoplasmic polyadenylation element binding protein, wherein a decrease in binding activity indicates the compound decreases RNA binding activity of human cytoplasmic polyadenylation element binding protein.

The present invention is also directed to a method of examining the reproductive potential of an oocyte, comprising the step of: determining the expression of human cytoplasmic polyadenylation element binding protein (hCPEB) in the oocyte, wherein the presence of human cytoplasmic polyadenylation element binding protein expression indicates the oocyte has reproductive potential, wherein the lack of human cytoplasmic polyadenylation element binding protein expression indicates the oocyte lacks reproductive potential.

In yet another aspect of the present invention, there is provided a method of selectively targeting gene expression in cells in vitro or specific organ tissues or regions in vivo under conditions of cytoplasmic polyadenylation element translational activation, comprising the steps of: (a) introducing mRNAs with cytoplasmic polyadenylation element sequence to said cells or tissues or regions and fusing with said gene; (b) introducing cytoplasmic polyadenylation element binding protein to said cells or tissues or regions; (c) challenging said cells or tissues or regions with specific stimuli, wherein said stimuli direct cytoplasmic polyadenylation element-mediated mRNA polyadenylation and translational activation of said gene in said cells or tissues or regions.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention as well as others which will become clear are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

FIGS. 1A–1H show human cytoplasmic polyadenylation element binding protein sequence and alignment comparison. FIGS. 1A–1G show hCPEB$_L$ cDNA sequence and predicted amino acid translation. Open arrowheads indicate the position of introns within the genomic human cytoplasmic polyadenylation element binding protein sequence and the closed arrowhead indicates the position of alternative splicing that yields the truncated hCPEB$_S$ variant. The predicted initiator methionine of hCPEB$_S$ is indicated. Methionine codons are underlined. An in-frame termination codon located 5' of the initiator methionine is indicated by an asterisk. The boundaries of the two RNA recognition motifs (RRM) and zinc finger domain (Znf) are bracketed. The two circled amino acids are putative Eg2 phosphorylation sites (Mendez et al., 2000). The unique BamHI site used to generate the DN-hCPEB protein is boxed.

FIG. 1H shows the first non-coding exon of hCPEB$_S$. Primers specific to the putative hCPEB$_S$ were used to amplify a region that lay upstream of the coding sequence. An in-frame termination codon that was identified 162 bp 5' of the initiator methionine is indicated by an asterisk. Methionine codons in the 5' UTR are underlined. The closed arrowhead is the alternative splice site shown in FIG. 1A. An intron of greater than 25 kb separates this first hCPEB$_S$ exon from the upstream hCPEB$_L$ exon 2.

FIG. 2A shows human multiple tissue northern blots were probed with the human cytoplasmic polyadenylation element binding protein cDNA isolated from HeLa cells. PBL, peripheral blood leukocytes; sk. muscle, skeletal muscle. An approximately 3300 nucleotide hCPEB mRNA is detected in ovary, brain and heart. The northern blot in the right panel has been exposed for twice the duration of the northern blot on the left to reveal human cytoplasmic polyadenylation element binding protein expression in the heart. FIG. 2B shows RT-PCR analysis of human cytoplasmic polyadenylation element binding protein expression in immature human oocytes. Total RNA was prepared from two germinal vesicle intact immature human oocytes using STAT-60 (Tel-test) and RT-PCR performed in a single tube using 0.4 oocyte equivalents of total RNA and the primers (+) AGATG GGGGT AGGGT CTCGG A (SEQ ID NO. 5) and (−) GCAGC TTGTC GGTGC AGCCT G (SEQ ID NO. 6) to amplify a 180 bp product (oocyte RNA). Reverse transcription was performed at 60° C. followed by PCR amplification using 35 cycles of 94° C. for 30 s; 60° C. for 30 s; and 68° C. for 45 s. As specificity controls, PCR amplification was performed using 0.4 oocyte equivalents of total RNA but without prior reverse transcription (oocyte RNA, RT 2). No product was obtained indicating that the PCR product was not a result of amplification from any contaminating genomic DNA in the RNA preparation. Similarly, no product was amplified when water was used as template instead of RNA sample (water). As a positive control, RT-PCR was performed using HeLa RNA as template.

FIG. 4A is a schematic representation of the wild type (wt) and mutant (mut) Xenopus-Mos 3' UTR utilized as probes for gel shift analyses. The mut UTR probe encodes a two nucleotide substitution within the CPE sequence. The position of the polyadenylation hexanucleotide (Hex) AAUAAA is also shown. FIG. 4B shows GST DN-hCPEB and the GST moiety alone were expressed in rabbit reticulocyte lysates and used for gel shift analyses with a radiolabeled wild type Xenopus Mos UTR probe. A solid arrowhead indicates specific complex formation between the radiolabeled probe and each GST-hCPEB fusion protein. The position of free probe is indicated. The GST DN-hCPEB/wt UTR complex was abolished using 50-fold excess unlabelled wt UTR probe but not with 50-fold excess unlabelled mut UTR probe. The GST DN-hCPEB/wt UTR complex could be supershifted with GST antiserum, but not with antiserum to B-Raf (open arrowhead). Several additional complexes were observed in the EMSA assay when incubated with unprogrammed reticulocyte lysate (UP) or GST moiety expressing lysate (open circles). However, these complexes were not supershifted by the GST antiserum and were competed by either unlabelled Mos wt UTR or mut UTR RNA, indicating that their formation was independent of the cytoplasmic polyadenylation element sequence or CPEB protein.

FIG. 5A is schematic representation of the position of candidate CPE sequences relative to the polyadenylation hexanucleotide sequence (HEX, AAUAAA). FIG. 5B shows sequence alignment comparison of primate and rodent Mos 3' UTR sequences. Candidate CPE sequences are circled, the polyadenylation hexanucleotide sequence is boxed.

FIG. 7A shows GST western blot to demonstrate the relative expression levels of the GST moiety or GST-hCPEB1 fusion protein in programmed rabbit reticulocyte lysates. The GST moiety alone was expressed to slightly higher levels than the GST-hCPEB1 fusion protein. UP, unprogrammed lysate. Arrowheads indicate position of the expressed proteins. FIG. 7B is schematic representation of the mutant human Mos 3' UTRs generated in this study. FIG. 7C shows RNA EMSA using a radiolabelled wild-type human Mos 3' UTR and either unprogrammed reticulocyte lysate (UP), or reticulocyte lysate programmed with mRNA encoding the GST moiety alone (GST) or an mRNA encoding a GST-hCPEB1 fusion protein. Where indicated, a 50 fold excess of unlabelled wild-type human Mos 3' UTR (Specific competitor) or a 50 fold excess of human Mos mutant 2 UTR (Non-specific competitor) RNA probe were also added to the binding reaction. The specific complex could be super shifted by addition of GST antiserum but not by addition of an irrelevant antiserum (B-Raf). FIG. 7D shows radiolabelled b-globin 3' UTR, wild-type human Mos 3' UTR, or various mutant human Mos 3' UTR probes (see FIG. 7B) were analyzed for interaction with the GST-hCPEB1 fusion protein by RNA EMSA as described for FIG. 7C. Specific complex formation was only observed with the wild-type and mutant 1 human Mos 3' UTR probes. For both FIGS. 7C and 7D, the position of the specific complex is indicated by an arrowhead, free probe by a filled circle and background non-specific complexes by an open circle. It should be noted that in the case of the mutant 1 UTR probe in (FIG. 7D, lane 5), an additional non-specific high molecular weight complex near the top of the gel was observed regardless of whether unprogrammed, GST moiety-alone or GST-hCPEB1 lysates were used. Representative results are shown.

FIG. 8A shows samples were analyzed for progesterone-dependent cytoplasmic polyadenylation by RNA-ligation coupled PCR. An increase in PCR product size is indicative of polyadenylation. In progesterone stimulated oocytes, the *Xenopus* Mos 3' UTR received an average of 40 adenylate residues and the human Mos 3' UTR received 32 adenylate residues. FIG. 8B shows a western blot analysis of protein lysates prepared from the same oocyte sample pool analyzed in FIG. 8A to visualize GST protein accumulation controlled by the indicated 3' UTR. GST protein levels were quantitated and the relative levels are indicated (normalized to the levels controlled by the b-globin 3' UTR in immature oocytes). The experiment was repeated three times with similar results.

DETAILED DESCRIPTION OF THE INVENTION

Figure 2A:
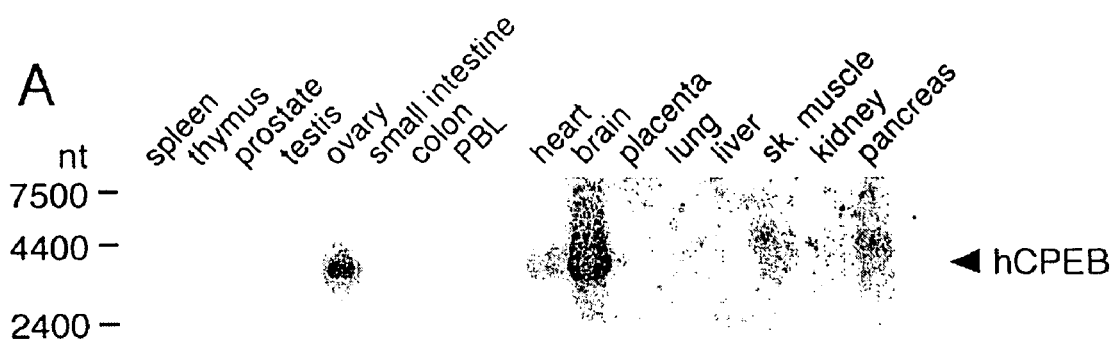
FIGS. 2A–2B shows human cytoplasmic polyadenylation element binding protein expression patterns in adult human tissue.

The following abbreviations are used herein: CPE; cytoplasmic polyadenylation element. CPEB; cytoplasmic polyadenylation element binding protein; PRE; polyadenylation response element; GST; glutathione S-transferase; 3' UTR, 3' untranslated region; EMSA; electrophoretic mobility shift assay; MAP kinase, mitogen activated protein kinase; GVBD; germinal vesicle breakdown.

The present invention reports the cloning of a human cytoplasmic polyadenylation element binding protein, hCPEB, which has CPE-specific RNA binding activity. The human cytoplasmic polyadenylation element binding protein is highly related to the cytoplasmic polyadenylation element binding proteins which have been previously cloned from frogs, mice, zebrafish and clams (Hake and Richter, 1994; Gebauer and Richter, 1996; Bally-Cuif et al., 1998; Walker et al., 1999). These proteins are all particularly conserved within the C-terminal RNA binding domain. Similar to the *Xenopus* and murine cytoplasmic polyadenylation element binding protein mRNAs, the hCPEB mRNA is expressed in immature oocytes (FIG. 2B) consistent with a presumptive role for the human cytoplasmic polyadenylation element binding protein in the translational regulation of mRNA in these cells. The present invention also reports that the human Mos 3' untranslated region (3' UTR) contains a functional cytoplasmic polyadenylation element (CPE), interacts with the human CPEB1 protein and directs maturation-dependent cytoplasmic polyadenylation of the endogenous Mos mRNA.

The human cytoplasmic polyadenylation element binding protein mRNA is subject to alternative splicing and is predicted to yield products that encode cytoplasmic polyadenylation element binding proteins with different N-terminal extensions. An mRNA for a short form of hCPEB (hCPEB$_S$) which encodes an N-terminally truncated protein lacking the first conserved homology domain (CHD1) was identified. The hCPEB$_S$ mRNA is expressed in ovary, brain and heart.

An alternatively spliced, long form of hCPEB (hCPEB$_L$) was also expressed in these tissues and encoded the N-terminal CHD1 region found in cytoplasmic polyadenylation element binding proteins from other vertebrate species (see FIG. 1B). Since both human cytoplasmic polyadenylation element binding protein mRNA splice variants contain multiple AUG codons in their 5' UTRs and consequently may be subject to mRNA translational regulation, it will be particularly interesting to determine whether the presence of human cytoplasmic polyadenylation element binding protein mRNA directly correlates with human cytoplasmic polyadenylation element binding protein expression in human tissues.

In accordance with the present invention there may be employed conventional molecular biology, microbiology, and recombinant DNA techniques within the skill of the art. Such techniques are explained fully in the literature. See e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

The invention includes a substantially pure DNA encoding a human cytoplasmic polyadenylation element binding protein. Preferably, the DNA includes the coding sequence of the nucleotides of SEQ ID NOs: 1 or 2, or a degenerate variant of such sequences. The present invention encompasses DNA that have at least about 70% sequence identity to the coding sequence of the nucleotides listed in SEQ ID NOs: 1 or 2, preferably at least 75% (e.g. at least 80%); and most preferably at least 90%.

"Substantially pure DNA" is DNA that is part of a milieu in which the DNA does not naturally occur. The DNA can be obtained by virtue of separation (partial or total purification) of some or all of the molecules of that milieu, or by virtue of alteration of sequences that flank the claimed DNA. The term therefore includes, for example, a recombinant DNA which is incorporated into a vector, an autonomously replicating plasmid or virus, the genomic DNA of a prokaryote or eukaryote; or which exists as a separate molecule (e.g., a cDNA, a genomic or cDNA fragment produced by polymerase chain reaction (PCR) or restriction endonuclease digestion) independent of other sequences. It also includes a recombinant DNA which is part of a hybrid gene encoding additional polypeptide sequence, e.g., a fusion protein. Also included is a recombinant DNA which includes a portion of the nucleotides listed in SEQ ID NO: 1 which encodes an alternative splice variant of human cytoplasmic polyadenylation element binding protein.

The invention also includes DNA that hybridizes at high stringency to a probe containing at least 15 consecutive nucleotides of SEQ ID NOs: 1 or 2. The probe to which the DNA of the invention hybridizes preferably consists of a sequence of at least 20 consecutive nucleotides, more preferably 40 nucleotides, even more preferably 50 nucleotides, and most preferably 100 nucleotides or more (up to 100%) of the coding sequence of the nucleotides listed in SEQ ID NOs: 1 or 2, or the complement thereof. Such a probe is useful for detecting expression of human cytoplasmic polyadenylation element binding protein in a cell by a method including the steps of (a) contacting mRNA obtained from the cell with the labeled hybridization probe; and (b) detecting hybridization of the probe with the mRNA.

By "high stringency" is meant DNA hybridization and wash conditions characterized by high temperature and low salt concentration, e.g., wash conditions of 65° C. at a salt concentration of approximately 0.1×SSC, or the functional equivalent thereof. For example, high stringency conditions may include hybridization at about 42° C. in the presence of about 50% formamide; a first wash at about 65° C. with about 2×SSC containing 1% SDS; followed by a second wash at about 65° C. with about 0.1×SSC.

The present invention further comprises a vector comprising a DNA sequence which encodes a human cytoplasmic polyadenylation element binding protein and said vector comprises in operable linkage: a) an origin of replication; b) a promoter; and c) a DNA sequence coding for said protein. Preferably, the vector of the present invention contains a portion of the DNA sequence shown in SEQ ID Nos: 1 or 2.

A "vector" may be defined as a replicable nucleic acid construct, e.g., a plasmid or viral nucleic acid. Vectors may be used to amplify and/or express nucleic acid encoding human cytoplasmic polyadenylation element binding protein. An "expression vector" is a replicable construct in which a nucleic acid sequence encoding a polypeptide is operably linked to suitable control sequences capable of effecting expression of the polypeptide in a cell. The need for such control sequences will vary depending upon the cell selected and the transformation method chosen. Generally, control sequences include a transcriptional promoter and/or enhancer, suitable mRNA ribosomal binding sites, and sequences which control the termination of transcription and translation. Methods which are well known to those skilled in the art can be used to construct expression vectors containing appropriate transcriptional and translational control signals. See for example, the techniques described in Sambrook et al., 1989, *Molecular Cloning: A Laboratory Manual* (2nd Ed.), Cold Spring Harbor Press, N.Y. A gene and its transcription control sequences are defined as being "operably linked" if the transcription control sequences effectively control the transcription of the gene. Vectors of the invention include, but are not limited to, plasmid vectors and viral vectors. Preferred viral vectors of the invention are those derived from retroviruses, adenovirus, adeno-associated virus, SV40 virus, or herpes viruses.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

As used herein, the term "host" is meant to include not only prokaryotes but also eukaryotes such as yeast, plant and animal cells. A recombinant DNA molecule or gene which encodes a human cytoplasmic polyadenylation element binding protein of the present invention can be used to transform a host using any of the techniques commonly known to those of ordinary skill in the art. Prokaryotic hosts may include *E. coli, S. tymphimurium, Serratia marcescens* and *Bacillus subtilis*. Eukaryotic hosts include yeasts such as *Pichia pastoris*, mammalian cells and insect cells.

Further included in this invention are substantially pure human cytoplasmic polyadenylation element binding protein (hCPEB) which are encoded at least in part by portions of SEQ ID NOs: 1 or 2, or encoded by products of alternative mRNA splicing or alternative protein processing events, or in which a section of human cytoplasmic polyadenylation element binding protein sequence has been deleted.

By a "substantially pure protein" is meant a protein which has been separated from at least some of those components which naturally accompany it. Typically, the protein is substantially pure when it is at least 60% by weight free from the proteins and other naturally-occurring organic molecules with which it is naturally associated in vivo. Preferably, the purity of the preparation is at least 75%, more preferably at least 90%, and most preferably at least 99%, by weight. A substantially pure human cytoplasmic polyadenylation element binding protein may be obtained, for example, by extraction from a natural source; by expression of a recombinant nucleic acid encoding a human cytoplasmic polyadenylation element binding protein polypeptide; or by chemically synthesizing the protein. Purity can be measured by any appropriate methods generally known to those of skill in the art. A protein which is chemically synthesized or produced in a cellular system different from the cell from which it naturally originates will be, by definition, substantially free from its naturally associated components. Accordingly, substantially pure proteins include eukaryotic proteins synthesized in *E. coli*, other prokaryotes, or any other organism in which they do not naturally occur.

In addition to substantially full-length proteins, the invention also includes fragments (e.g., antigenic fragments) of the human cytoplasmic polyadenylation element binding protein (hCPEB, SEQ ID Nos: 3 or 4). As used herein, "fragment," as applied to a polypeptide, will ordinarily be at least 10 residues, more typically at least 20 residues, and preferably at least 30 (e.g., 50) residues in length, but less than the entire, intact sequence. Fragments of the human cytoplasmic polyadenylation element binding protein can be generated by methods known to those skilled in the art, e.g., by enzymatic digestion of naturally occurring or recombinant human cytoplasmic polyadenylation element binding protein, by recombinant DNA techniques using an expression vector that encodes a defined fragment of human cytoplasmic polyadenylation element binding protein, or by chemical synthesis. The ability of a candidate fragment to exhibit a characteristic of human cytoplasmic polyadenylation element binding protein (e.g., binding to cytoplasmic polyadenylation element sequence) can be assessed by methods described herein.

The fragment, or the intact human cytoplasmic polyadenylation element binding protein polypeptide, may be covalently linked to another polypeptide, e.g. which acts as a label, a ligand or a means to increase antigenicity. Purified human cytoplasmic polyadenylation element binding protein or antigenic fragments thereof can be used to generate new antibodies or to test existing antibodies (e.g., as positive controls in a diagnostic assay) by employing standard protocols known to those skilled in the art. Any such antibody so generated, or a fragment thereof, may be linked to a toxin or to a detectable label generally known in the art, e.g. a radioactive label, non-radioactive isotopic label, fluorescent label, chemiluminescent label, paramagnetic label, enzyme label, or colorimetric label. Examples of suitable toxins include diphtheria toxin, *Pseudomonas* exotoxin A, ricin, and cholera toxin. Representative examples of suitable radioisotopic labels include $^3$H, $^{125}$I, $^{131}$I, $^{32}$P, $^{35}$S, $^{14}$C, etc.

The present invention provides a number of diagnostic advantages and uses. Given the potential key role of human cytoplasmic polyadenylation element binding protein (hCPEB) in the control of mRNA translation in cells such as oocytes and neurons, expression of human cytoplasmic polyadenylation element binding protein can be a diagnostic tool for assessing reproductive potential (e.g. infertility or low fertility) or brain functions such as learning, memory and cognitive functions. On the other hand, mutant forms of the human cytoplasmic polyadenylation element binding protein that have altered RNA binding activities can be used to modulate fertility and brain functions. Moreover, drugs can be targeted to block activated human cytoplasmic polyadenylation element binding protein functions in germ line and somatic tissue (e.g. brain) for the treatment of various disorders.

Antibodies (or antigen-binding fragments thereof) which bind to an epitope specific for human cytoplasmic polyadenylation element binding protein are useful in methods of detecting human cytoplasmic polyadenylation element binding protein in a biological sample. This method includes the steps of obtaining a biological sample (e.g. oocytes or brain cells), contacting the sample with a labeled antibody (e.g., radioactively tagged antibody) specific for human cytoplasmic polyadenylation element binding protein, and detecting the human cytoplasmic polyadenylation element binding protein using standard immunoassay techniques such as an ELISA. Likewise, a standard Northern blot assay can be used to ascertain the relative amounts of human cytoplasmic polyadenylation element binding protein mRNA in a cell or tissue in accordance with conventional Northern hybridization techniques known to those persons of ordinary skill in the art.

The present invention is directed to an isolated DNA encoding human cytoplasmic polyadenylation element binding protein, expression vectors that contain the claimed DNA, as well as host cells that contains the expression vectors. The claimed DNA includes DNA that has the sequence of SEQ ID No. 1 or 2, or DNA that encodes human cytoplasmic polyadenylation element binding protein but differs from SEQ ID No. 1 or 2 in codon sequence due to degeneracy of the genetic code. The host cell can be bacterial cells, mammalian cells, plant cells or insect cells. The present invention further encompasses an isolated DNA which is complementary to the DNA disclosed herein.

The present invention also provides a recombinant human cytoplasmic polyadenylation element binding protein and polypeptides derived thereof. The human cytoplasmic polyadenylation element binding protein has the amino acid sequence of SEQ ID No. 3 or 4, and the polypeptide has at least 10 amino acid residues.

In another aspect of the present invention, there is provided a method of screening for compound that increases or decreases the RNA binding activity of human cytoplasmic polyadenylation element binding protein (hCPEB). The method involves the steps of (a) contacting human cytoplasmic polyadenylation element binding protein with a probe comprising cytoplasmic polyadenylation element (CPE) sequence in the presence of said compound; and (b) determining the cytoplasmic polyadenylation element sequence-specific binding activity of the human cytoplasmic polyadenylation element binding protein, wherein an increase in binding activity indicates said compound increases RNA binding activity of human cytoplasmic polyadenylation element binding protein, wherein a decrease in binding activity indicates said compound decreases RNA binding activity of human cytoplasmic polyadenylation element binding protein.

The present invention is also directed to a method of examining the reproductive potential of an oocyte, comprising the step of: determining the expression and/or activity of human cytoplasmic polyadenylation element binding protein (hCPEB) in said oocyte, wherein the presence of human cytoplasmic polyadenylation element binding protein expression or activity indicates said oocyte has reproductive potential, wherein the lack of human cytoplasmic polyadenylation element binding protein expression or activity indicates said oocyte lacks reproductive potential.

In yet another aspect of the present invention, there is provided a method of selectively targeting gene expression in cells in vitro or specific organ tissues or regions in vivo under conditions of cytoplasmic polyadenylation element translational activation, comprising the steps of: (a) introducing mRNAs with cytoplasmic polyadenylation element sequence to said cells or tissues or regions and fusing with said gene; (b) introducing cytoplasmic polyadenylation element binding protein to said cells or tissues or regions; (c) challenging said cells or tissues or regions with specific stimuli, wherein said stimuli direct cytoplasmic polyadenylation element-mediated mRNA polyadenylation and translational activation of said gene in said cells or tissues or regions.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Plasmids Constructs and RNA Synthesis

Plasmid pGEM XeMos wt UTR was constructed as follows. The terminal 321 nucleotides of the Mos 3' UTR was cloned from immature oocytes by reverse transcription polymerase chain reaction (RT-PCR) to make pGEM Mos 321 UTR (Howard et al., 1999). A primer with a 5' BamHI site (+) GCGGG ATCCA TTCCA TATGT GAATA TATAG (SEQ ID NO. 11) was designed to amplify the last 48 nucleotides of the Mos 3' UTR from pGEM Mos 321 UTR. The reverse primer was the T7 promoter primer TAATA CGACT CACTA TAGGG (SEQ ID NO. 12). The PCR product was cut with BamHI/HindIII and inserted into BamHI/HindIII digested pGEM4Z. The size of the probe after in vitro transcription with SP6 RNA polymerase was 82 nt (48 nt that correspond to Mos UTR, and 34 nt that derive from the pGEM polylinker). The integrity of the probe was confirmed by DNA sequencing.

Plasmid pGEM XeMos mut UTR was constructed as follows. The terminal 321 nucleotides of the Mos 3' UTR was cloned from immature oocytes by RT-PCR. PCR primers were designed to include 5' BamHI (+) CGCGG ATCCC CCGGG CACTA GTAGC CAGGA GTTCA T (SEQ ID NO. 13) and 3' XbaI (−) CGTCT AGACA AATCA ATTTC TTTAT TACCA AACTA TATAT TC (SEQ ID NO. 14) restriction sites. The 3' (−) primer substituted a mutant CPE sequence, TTTggT, for the wild type TTTTAT. The resulting PCR product was cloned into BamHI/XbaI digested pGEM4Z (Promega) and designated pGEM Mos M3. The integrity of the Mos UTR was confirmed by DNA sequencing. The mutant EMSA probe was made from the pGEM Mos M3 template using the same strategy and primers as for the wild type probe above. The integrity of the probe was confirmed by DNA sequencing.

For in vitro transcription to generate radiolabeled RNA gel shift probes, pGEM XeMos wt UTR and pGEM XeMos mut UTR were linearized with XbaI, transcribed with the SP6 RNA polymerase (Melton et al., 1984) and 50 mM UTP, 0.5 mM ATP, 0.5 mM CTP, 0.5 mM GTP and 50 mCi of [a-$^{32}$P]UTP (400 Ci/mmol, Amersham).

EXAMPLE 2

Northern and Southern Blot Analyses

Human multiple tissue northern blots (2 mg polyA+RNA per lane) (Clontech) were probed with a 1326 bp BamHI/XcmI fragment of clone H12139 radioactively labeled using the random primer labeling kit (Pharmacia) and [a-$^{32}$P] dCTP (Amersham). Following overnight hybridization at 55° C., the membranes were washed twice in 1×SSC (0.15 M NaCl, 0.015 M sodium citrate)—0.5% SDS for 10 min at 55° C. and twice in 0.1×SSC—0.1% SDS for 30 min at 55° C. and analyzed by autoradiography. For Southern analysis, 10 ug of human genomic DNA was digested with the indicated enzymes, transferred to nitrocellulose and probed with a multimerized probe corresponding to nucleotides 543–765 of hCPEB$_L$. Filters were washed twice with 2×SSC, 0.1% SDS for 10 min at room temperature and twice 0.1×SSC, 0.1% SDS for 30 min at 65° C. and analyzed by autoradiography.

EXAMPLE 3

Human Oocyte Harvest and RT-PCR Analysis

Germinal vesicle-intact human oocytes were collected from consenting patients following a protocol approved by the Institutional Review Board at the University of Michigan. Oocyte-cumulus masses were collected into HEPES-buffered human tubule fluid media containing 3% (vol/vol) human serum albumin (HTF-H3; Irvine Scientific, Santa Ana, Calif.) by transvaginal follicular aspiration after controlled ovarian stimulation (Pool and Martin, 1994). Cumulus and corona radiata cells were removed by brief exposure to HTF-H3 containing 80 IU hyaluronidase (Sigma, St. Louis, Mo.) followed by mechanical pipetting through flame-pulled Pasteur pipettes. Complete absence of non-gamete cells and presence of germinal vesicle were confirmed using an inverted microscope with Hoffman optics at 400×. Germinal vesicle-intact oocytes were pooled, frozen in liquid nitrogen and stored at −80° C. until analyses were performed. RT-PCR was performed as described below.

EXAMPLE 4

RNA Electrophoretic Mobility Shift Assays (EMSA)

An N-terminally truncated form of human cytoplasmic polyadenylation element binding protein that was common to both splice variants, (GST DN-hCPEB), was generated for analysis of hCPEB sequence-specific RNA binding activity. Clone H12139, in Lafmid BA vector, was digested with NarI (located 27 bp downstream of the termination codon in the hCPEB 3' UTR), blunted with Klenow, and digested with BamH1 to yield a 1288 bp fragment, DN-hCPEB. This was then ligated in-frame to the N-terminal GST moiety of the pXen1 expression vector (MacNicol et al., 1997) to generate pXen DN-hCPEB. Protein for EMSA experiments was prepared by coupled transcription/translation using SP6 RNA polymerase (Promega), non-radioactively labeled methionine and a rabbit reticulocyte lysate system (TNT Coupled System, Promega) according to the manufacturer's protocol. GST DN-human cytoplasmic polyadenylation element binding protein levels were normalized relative to the level of the GST moiety expressed alone by anti-GST Western blotting and densitometry. The GST moiety was expressed from the pXen1 vector lacking any insert. EMSA binding reactions, competition experiments and supershift assays were performed as previously described (Charlesworth et al., 2000).

EXAMPLE 5

Identification of the Gene Encoding the Human Cytoplasmic Polyadenylation Element Binding Protein (hCPEB)

Human EST's with homology to the *Xenopus* CPEB cDNA were identified in GenBank using BLAST (Altschul et al., 1997). Three cDNA clones H12139, N54198 and AA323191 were sequenced completely and found to encode partially overlapping sequence. These sequences contained a 491 amino acid open reading frame predicted to encode a protein of approximately 55 kD. 5' RACE was used to obtain extended human CPEB sequence from Marathon-Ready human ovary cDNA (Clontech) using an hCPEB-specific reverse primer (5' (–) GGGGA TCCAG AGGCA GGAAG CTCAA, SEQ ID NO. 15). Multiple independent cDNA clones representing two alternative 5' sequences were obtained and designated hCPEB short (hCPEB$_S$) and hCPEB long (hCPEB$_L$). A subsequent BLAST search of the human genome sequence (NCBI) identified three overlapping contigs that matched the hCPEB$_L$ and hCPEB$_S$ cDNA sequences (GenBank AC010724; AC011140 and AC068126).

Analysis of the human genomic sequence revealed the presence of 14 exons spanning greater than 54 kb. The genomic sequence identified the first exon sequence of hCPEB$_L$ included the first five amino acids with a predicted initiator methionine and was separated from the exon encoding amino acids six through 63 by a 771 bp intron. Characterization of intron/exon boundaries revealed that the hCPEB$_L$ and hCPEB$_S$ sequences arise as a consequence of alternative splicing (FIGS. 1A–1G). The sequences of human cytoplasmic polyadenylation element binding protein long (AF329402) and human cytoplasmic polyadenylation element binding protein short (AF329403) have been submitted to GenBank.

An alignment of the human cytoplasmic polyadenylation element binding protein genomic sequence with the known cDNA sequences of murine, *Xenopus* and zebrafish (Hake and Richter, 1994; Gebauer and Richter, 1996; Bally-Cuif et al., 1998) allowed us to delimit the N-terminus of hCPEB$_L$. While the N-terminal domain of CPEB is less well conserved between species than the C-terminal domain, three blocks of homology (CPEB homology domain, CHD) are apparent. CHD1 spans amino acids 22–53 of the hCPEB$_L$ protein; CHD2 spans amino acids 87–118; CHD3 spans amino acids 168–214 (FIGS. 1A–1C).

A short form of CPEB has not been previously described. To establish that hCPEB$_S$ represented a naturally occurring mRNA, a cDNA encoding this protein was amplified via RT-PCR from human ovary RNA and HeLa cells. DNA sequencing (FIG. 1A, 1H) confirmed the presence of an in-frame stop codon, 162 bp upstream of the putative initiator methionine. When compared to the murine, *Xenopus* and zebrafish cDNA sequences, the predicted hCPEB$_S$ protein lacked 75, 76 and 74 N-terminal amino acids respectively, suggesting that this is a truncated form of the cytoplasmic polyadenylation element binding protein. The predicted hCPEB$_S$ protein lacks CHD1 but contains CHD2 which is serine and leucine rich. The hCPEB$_S$ also contains CHD3 which is serine, proline and glycine rich and encodes sites of proposed regulatory phosphorylation (Mendez et al., 2000) and a region resembling a PEST degradation sequence (Rechsteiner and Rogers, 1996).

Alignment of the hCPEB$_S$ and hCPEB$_L$ cDNA with the human cytoplasmic polyadenylation element binding protein genomic sequence revealed that alternative splicing generates the hCPEB$_L$ and hCPEB$_S$ mRNA species. Interestingly, the 5' UTR of both hCPEB mRNA splice variants encode multiple upstream AUG codons (FIG. 1A, 1H), suggesting that the translation of the hCPEB$_L$ and hCPEB$_S$ mRNAs may be tightly regulated (reviewed in Gray and Wickens, 1998). The 5' UTR of hCPEB$_L$ contains five in-frame AUG codons (FIG. 1A, doubly underlined) between the upstream in-frame STOP codon and the predicted initiator methionine of hCPEB$_L$, raising the possibility that alternative initiator AUG utilization may produce hCPEB$_L$ protein variants with different N-terminal amino acid sequence. The other six AUG codons initiate short open reading frames that terminate within the hCPEB$_L$ 5' UTR prior to the predicted initiator methionine. All upstream AUG codons in the hCPEB$_S$ 5' UTR are in alternative reading frames. No upstream AUG codons are found in the 5' UTRs of the frog, zebrafish or mouse CPEB mRNAs, although the reported mouse 5' UTR is likely incomplete (Gebauer and Richter, 1996). While the zebrafish CPEB mRNA lacks upstream AUGs, it may be subject to translational regulation since the 3' UTR contains a cytoplasmic polyadenylation element sequence (Bally-Cuif et al., 1998).

To determine if human cytoplasmic polyadenylation element binding protein was part of a multi-gene family, a region common to both human cytoplasmic polyadenylation element binding protein mRNA splice variants was used to probe restriction enzyme digested human genomic DNA. Single cross-reacting fragments, a 6 kb BamHI and a 2.8 kb BamHI/BglII fragment, were identified, suggesting that human cytoplasmic polyadenylation element binding protein may be encoded by a single gene. Consistent with this interpretation, no additional human genome sequence contigs that had significant homology to human cytoplasmic polyadenylation element binding protein were identified in the NCBI database.

A comparison of the predicted amino acid sequence of the hCPEB$_L$ protein revealed an overall 95% identity to mouse cytoplasmic polyadenylation element binding protein, with particularly high homology between the RNA recognition motifs (RRMs) and the C-terminal zinc finger motif (Znf). Similar to the *Xenopus* protein, the hCPEB$_L$ protein ends with RDSS, a sequence deleted in the murine cytoplasmic polyadenylation element binding protein (Gebauer and Richter, 1996). Both hCPEB$_L$ and hCPEB$_S$ isoforms contain two conserved putative Eg2 phosphorylation sites (Mendez et al., 2000) (FIG. 1C, circled), although the first Eg2 motif encodes threonine instead of the serine residue found in *Xenopus* CPEB.

EXAMPLE 6

Expression of the Human CPEB mRNA in Human Tissues

To determine the expression pattern of the human cytoplasmic polyadenylation element binding protein homologue, multiple tissue northern blots were probed with radiolabeled hCPEB cDNA corresponding to the C-terminal half of the coding region which is identical in both hCPEB$_L$ and hCPEB$_S$ mRNAs. High levels of hCPEB mRNA were detected in adult ovary and brain with lower levels detected in the heart (FIG. 2A). The difference in size between the hCPEB cDNA sequences and the mRNA species detected in these tissues may be due to extended 5' UTR sequence. Cytoplasmic polyadenylation element binding protein cross-reactive bands were also detected in pancreas and skeletal muscle but are larger than the species detected in ovary, heart and brain. These larger bands may derive from the alternative splicing of additional, as yet uncharacterized, human cytoplasmic polyadenylation element binding protein exons or may derive from an as yet unidentified human cytoplasmic polyadenylation element binding protein-related gene.

Figure 2B:
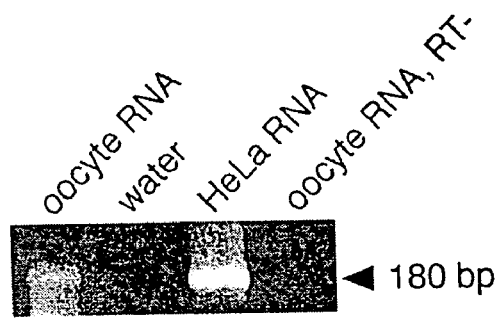

It has been previously demonstrated that the *Xenopus* and murine cytoplasmic polyadenylation element binding protein mRNAs are expressed in immature oocytes (Hake and Richter, 1994; Gebauer and Richter, 1996). To determine if human cytoplasmic polyadenylation element binding protein was expressed in immature human oocytes, RT-PCR analysis was performed using a PCR primer combination that does not discriminate between the long and short forms of human cytoplasmic polyadenylation element binding protein. As can be seen in FIG. 2B, hCPEB mRNA is indeed expressed in immature human oocytes.

Figure 3:
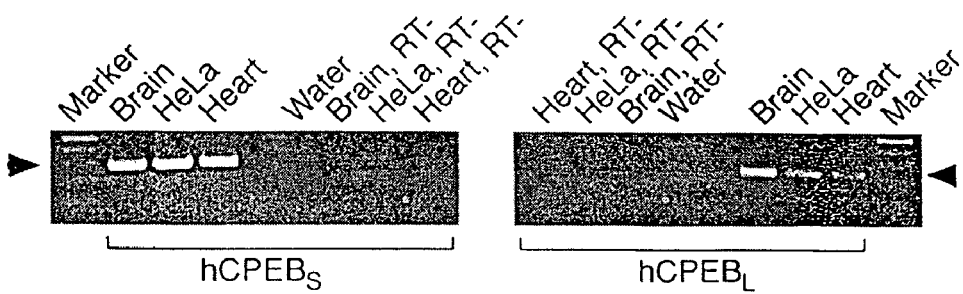
FIG. 3 shows alternatively spliced forms of human cytoplasmic polyadenylation element binding protein expressed in brain and heart. For analysis of differential expression of hCPEB$_L$ and hCPEB$_S$ mRNAs, 200 ng of human brain, heart or HeLa cell total RNA were reverse transcribed using either hCPEB$_L$ (−) GCATC CTGCT TGTAA CTGTT (SEQ ID NO. 7) or hCPEB$_S$ (−) GGACT GCAGG CCAAG GCA (SEQ ID NO. 8). Subsequent PCR amplification of the long form of human cytoplasmic polyadenylation element binding protein was obtained using both the hCPEB$_L$ (−) primer and hCPEB$_L$ (+) GGAAG AAGAA GCAGG AAGGA T (SEQ ID NO. 9) to amplify a 215 bp product (right panel). For PCR amplification of the short form of human cytoplasmic polyadenylation element binding protein, both the hCPEB$_S$ (−) primer and hCPEB$_S$ (+) GCGGA ATTCC AGCGG GAAGC ATCAG CAG (SEQ ID NO. 10) were used to amplify a 283 bp product (left panel). PCR parameters were the same for both hCPEB$_L$ and hCPEB$_S$ primer pairs: 35 cycles of 94° C. for 30 seconds; 40° C. for 30 seconds; and 72° C. for 48 seconds. As controls for specificity, PCR amplification was performed without prior reverse transcription (RT-) and in all cases no PCR product was obtained. Similarly, no product was amplified when water was used as template instead of RNA sample (water). All PCR products were sequenced to verify the integrity of the amplified region of human cytoplasmic polyadenylation element binding protein.

When PCR primers specific for the hCPEB$_L$ and hCPEB$_S$ isoforms were utilized, it was found that both the hCPEB$_L$ and hCPEB$_S$ splice variants are expressed in human brain and heart tissue as well as in the HeLa cell line (FIG. 3). The RT-PCR data suggest that the hCPEB$_L$ mRNA may be preferentially expressed in the brain, whereas the hCPEB$_S$ transcript does not show any appreciable difference in levels between brain and heart tissue.

The expression of mRNA encoding human cytoplasmic polyadenylation element binding protein in human brain is interesting in light of a recent study which suggests that cytoplasmic polyadenylation element-regulated mRNA translational control may function in the brain. Specifically, cytoplasmic polyadenylation element sequences and the cytoplasmic polyadenylation element binding protein have been implicated in the control of CaMKIIa mRNA cytoplasmic polyadenylation and translation during long term potentiation in the rat hippocampus (Wu et al., 1998). No human mRNAs have yet been identified which contain functional cytoplasmic polyadenylation element sequences. However, a survey of vertebrate 3' UTRs suggest that potential cytoplasmic polyadenylation element sequences exist in a variety of human mRNAs (Pesole et al., 2000), including some mRNAs implicated in regulating oocyte maturation (e.g. Raf-1, Wee1) and neuronal function (e.g. FGF receptor 1, PTPz).

EXAMPLE 7

Human CPEB is a Sequence Specific RNA Binding Protein

To determine if human cytoplasmic polyadenylation element binding protein possessed cytoplasmic polyadenylation element-sequence specific RNA binding activity, human cytoplasmic polyadenylation element binding protein was incubated with a radiolabeled RNA probe corresponding to the terminal 48 nucleotides of the wild-type *Xenopus* Mos 3' UTR (wt UTR, FIG. 4A) and binding was determined in an electrophoretic mobility shift assay (EMSA). The *Xenopus* Mos 3' UTR was used to characterize hCPEB RNA binding properties since it has previously been shown to interact with the heterologous murine cytoplasmic polyadenylation element binding protein as well as the *Xenopus* CPEB (Gebauer and Richter, 1996; Stebbins-Boaz et al., 1996).

For these experiments, an N-terminal deletion of hCPEB (DN hCPEB) which contains all the characterized RNA interaction domains and possesses sequence common to both the hCPEB$_L$ and hCPEB$_S$ splice variants was utilized. The DN human cytoplasmic polyadenylation element binding protein was expressed as an in-frame fusion to an N-terminal GST epitope tag following in vitro transcription and translation in rabbit reticulocyte lysates. The GST moiety expressed alone or unprogrammed lysate (UP) was also utilized to enable a distinction between non-specific and specific interactions with the Mos 3' UTR probe.

Figures 4A, 4B:
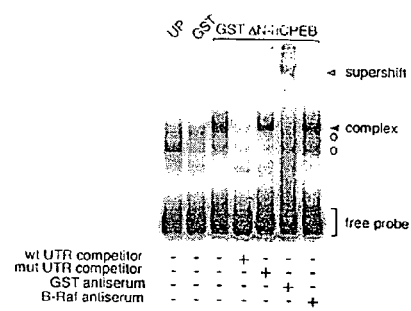
FIGS. 4A–4B shows human cytoplasmic polyadenylation element binding protein is a sequence-specific RNA binding protein.

As shown in FIG. 4B, the DN hCPEB protein formed a specific complex with the Mos UTR probe. Specific complexes did not form with the GST moiety alone or unprogrammed lysate (UP). Complex formation was dependent upon the cytoplasmic polyadenylation element sequence within the Mos UTR probe because addition of a 50-fold excess of unlabelled 3' UTR effectively competed GST DN hCPEB interaction with radiolabeled Mos UTR. In contrast, a 50-fold excess of unlabelled mutant 3' UTR encoding a 2 nucleotide substitution within the CPE (FIG. 4A, mut UTR) did not compete GST DN hCPEB/Mos UTR binding (FIG. 4B). The presence of human cytoplasmic polyadenylation element binding protein in the specific Mos UTR complexes was verified by a supershift analysis. Antiserum against the N-terminal GST tag effectively supershifted the GST DN hCPEB/Mos UTR complex (FIG. 4B). Antiserum against an unrelated protein, B-Raf, did not elicit a supershift of the hCPEB/Mos UTR complex (FIG. 4B).

The mechanism(s) by which the cytoplasmic polyadenylation element binding protein regulates mRNA translation has not been fully elucidated. The ability of cytoplasmic polyadenylation element binding protein to interact with cytoplasmic polyadenylation element-containing RNA target sequences has been shown to require the evolutionarily conserved C-terminal RNA recognition motifs and zinc finger domain (Hake et al., 1998). The cytoplasmic polyadenylation element binding protein is associated with cytoplasmic polyadenylation element-containing mRNAs in both immature and mature *Xenopus* oocytes (Hake and Richter, 1994; Stebbins-Boaz et al., 1996). The cytoplasmic polyadenylation element binding protein N-terminal domain may function to promote translational activation in maturing oocytes. This domain contains sites of maturation-dependent phosphorylation (Mendez et al., 2000) and a recent study has demonstrated that mutation of two N-terminal Eg2 phosphorylation sites or deletion of the first 139 amino acids of the N-terminal domain generates an inhibitory, dominant negative form of the *Xenopus* cytoplasmic polyadenylation element binding protein. These dominant negative cytoplasmic polyadenylation element binding proteins prevent translational activation and cytoplasmic polyadenylation but maintain cytoplasmic polyadenylation element-directed translational repression in maturing oocytes (Mendez et al., 2000). The predicted hCPEB$_S$ protein contains both the C-terminal RNA binding domain and the N-terminal sites of Eg2 regulatory phosphorylation. The absence of the CHD1 in hCPEB$_S$ domain may confer altered regulatory properties to the hCPEB$_S$ protein or alter the subcellular localization of the hCPEB$_S$ protein (Wu et al., 1998). Further characterization of the properties of the alternatively spliced forms of the human cytoplasmic polyadenylation element binding protein may provide insight into the role of the N-terminal domain of the cytoplasmic polyadenylation element binding protein in mediating mRNA translational control.

EXAMPLE 8

Human Mos 3' UTR Constructs and CPE Mutants

Construction of pGEM GST b-globin 3' UTR and pGEM GST XeMos 3' UTR has been described elsewhere (Charlesworth et al., 2000). pGEM GST hMos 3' UTR was constructed by amplifying the human Mos 3' UTR (119 bp) by PCR from Hela cells and cloned into BamHI and XbaI sites of pGEM GST (Charlesworth et al., 2000). The primers were designed to encode a 5' BamH1 site and a 3' Xba1 site: 5'(+) CGCGG ATCCT TAGCT GAAAA CCTGG TCAAG ATAAG (SEQ ID NO. 17) and 5'(−) CGGTC TAGAT AAAGG AGTTT TTAGT AACTT TATTT (SEQ ID NO. 18). The amplified hMos 3' UTR fragment encodes a 5' in-frame STOP codon (underlined) to terminate the GST open reading frame upstream of the Mos 3' UTR sequence. PCR mutagenesis of the hMos 3' UTR was performed using a QuikChange Site-Directed Mutagenesis kit as per manufacturer's instructions (Stratagene). All hMos 3' UTR mutations were verified by DNA sequence analysis.

EXAMPLE 9

EMSA Probes and EMSA

The GST fragment in the wild-type and mutant pGEM GST hMos 3' UTR plasmids was deleted by digesting with Nco 1 and Xho 1, klenow treated and blunt end ligated. The resulting plasmids, were used for the in vitro transcription of radiolabelled hMos 3' UTR EMSA probes as previously described (Charlesworth et al., 2000). Similarly, Nco 1/Xho 1 deletion of the GST fragment in pGEM GST b-globin 3' UTR generated a template for in vitro transcription of the b-globin 3' UTR EMSA probe. All EMSA reactions, unlabelled probe competition and antibody supershifts were as described in Example 4.

EXAMPLE 10

Human Oocyte Collection and RNA Extraction

Human immature (GV) and mature (MII) oocytes were obtained from the consented patients undergoing in vitro fertilization (IVF) and/or Intra Cytoplasmic Sperm Injection (ICSI) after standard ovarian stimulation (Mahadevan, et al., 1998). Oocytes were denuded with Hyaluronidase (Sigma, St Louis, Mo.) and mechanical pipetting. Oocytes were examined for nuclear maturity and classified as either mature (MII) or immature (GV). The oocytes were lysed in 500 ml of RNA Stat-60 and frozen immediately in liquid Nitrogen. Total RNA from these oocytes was extracted as follows: 100 ml of chloroform was added, mixed vigorously, incubated at room temperature for 3 min and the upper aqueous phase was colleted after centrifugation at 12000 g for 3 min. The RNA was precipitated by adding isopropanol, incubating at 4° C. for 30 min and subsequent centrifugation at 12000 g for 15 min at 4° C. Following a 70% ethanol wash, total RNA was resuspended in RNase-free water (2.5 ml/oocyte).

EXAMPLE 11

*Xenopus* Oocytes, mRNA Injections and Sample Preparation

*Xenopus* oocyte isolation and culture has been described (Machaca, et al., 2002). To analyze progesterone-inducible translation, GST reporter RNAs were normalized within each experimental set and injected at 0.05–0.1 ng of RNA per oocyte in order to reduce the background level of translation (Charlesworth et al., 2000). As indicated, oocytes were injected with in vitro transcribed RNA encoding a GST open reading framed fused to either the last 48 nucleotides of the *Xenopus* Mos 3' UTR (Charlesworth et al., 2002) or the indicated 119 nucleotide human Mos 3' UTR generated in this study. Oocytes were stimulated with 2 µg/ml progesterone (Sigma) and the rate of germinal vesicle breakdown (GVBD) monitored morphologically by the appearance of a white spot on the animal hemisphere. Pools of 5–10 oocytes were harvested and immature control samples were prepared at the same time as the progesterone-stimulated oocyte samples. For analysis of both protein and RNA from the same oocyte samples, pools of oocytes were rapidly lysed in Nonidet P-40 buffer as above and then a portion was removed and immediately mixed with RNA STAT-60 as previously described (Charlesworth et al., 2002). Results shown are representative experiments that were typically repeated 3 times with similar results.

EXAMPLE 12

Western Blot Analyses

Preparation of protein lysates and ECL western blot analyses were performed as previously described (Charlesworth et al., 2000). Rabbit polyclonal antibody against Glutathione S-Transferase (GST) (Z-5) was obtained from Santa Cruz Biotechnology, Inc. GST protein accumulation was quantitated using a ChemiImager 5500 and AlphaEaseFC software (AlphaInnotech Corp.).

EXAMPLE 13

RNA Ligation-Coupled PCR Polyadenylation Assays

The polyadenylation status of GST reporter or endogenous *Xenopus* Mos and cyclin A1 mRNAs were assessed by RNA ligation-coupled PCR (Rassa, et al., 2000) essentially as described previously (Charlesworth et al., 2002). Briefly, total RNA from *Xenopus* or human oocytes was isolated by RNA-STAT60 and a primer, P1, was ligated to the RNA 3' termini. Subsequently, reverse transcription was driven using a primer complementary to the ligated P1 anchor sequence (P1'). Standard PCR amplification was then performed using an appropriate forward primer specific to the GST or human Mos coding regions or the *Xenopus* Mos or cyclin A1 3' UTRs and the P1' reverse primer complementary to all ligated mRNAs in the sample. For the analysis of human Mos polyadenylation, 5 ml of cDNA (0.4 oocyte equivalents) was used with the Mos forward primer 5' CGGTT GCTCT GAGAA GTTGG AAGA (SEQ ID NO. 19), and reverse primer P1' (Rassa, et al., 2000). The PCR amplification conditions were: 94° C. for 2 min, and then 40 cycles of [94° C. for 30 sec, 56° C. 1 min, 72° C. for 1 min and 30 sec] and PCR products were analyzed on a 1.5% agarose gel.

EXAMPLE 14

Cloning and Sequence Characterization of the Human Mos 3' UTR

Figures 5A, 5B:
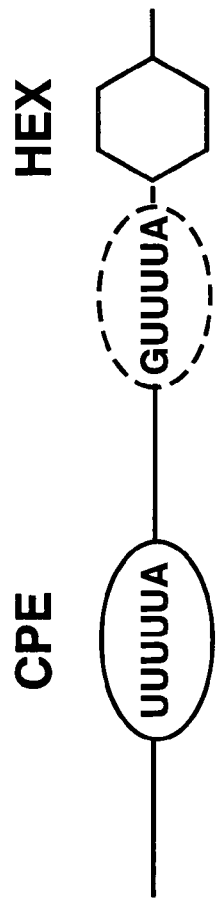
FIGS. 5A–5B shows the human Mos mRNA contains a cytoplasmic polyadenylation element (CPE).

While the cloning of the human Mos cDNA has been previously reported, the sequence included only 22 nucleotides of the 3' UTR and lacked a polyadenylation hexanucleotide (Watson, et al., 1982). Consequently, an assessment of the possible role of CPE-directed polyadenylation in the control of human Mos mRNA translational activation has not hitherto been addressed. The 3' UTR of the human Mos mRNA was amplified from both Hela cells and human oocyte total RNA by ligation-coupled PCR (Rassa, et al., 2000) and subjected to DNA sequence analysis (FIG. 5). The Mos 3' UTR sequence was identical from both sources. The entire 119 nucleotide human Mos 3' UTR was then cloned from Hela cells using UTR-specific PCR primers. Analysis of the human Mos 3' UTR sequence revealed a $U_5A$ CPE consensus sequence 5' of the polyadenylation hexanucleotide (FIG. 5A). A similar CPE sequence is present at the same position in the rodent Mos 3' UTRs (FIG. 5B) and has been shown to be a functional CPE in the murine Mos 3' UTR (Gebauer, et al., 1994). While the murine and rat Mos 3' UTRs contain a second $U_5A$ CPE sequence closer to the polyadenylation hexanucleotide (FIG. 5B), the human and monkey Mos 3' UTRs lack the 5'-most U and only retain a $U_4A$ sequence (FIG. 5A dashed oval). $U_4A$ sequences have not been previously shown to possess CPE function.

EXAMPLE 15

Figure 6:
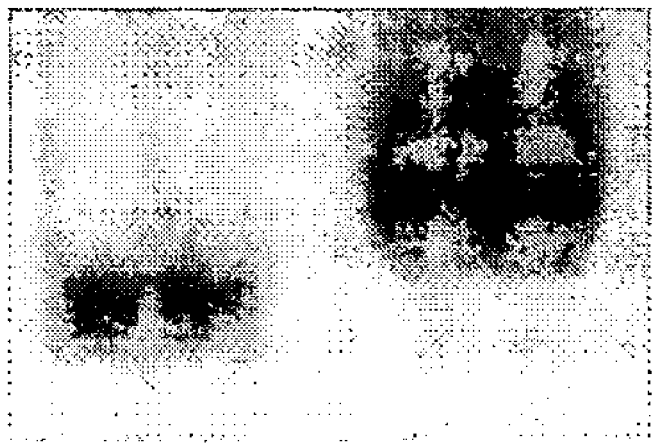
FIG. 6 shows the endogenous Mos mRNA undergoes maturation dependent cytoplasmic polyadenylation in human oocytes. Two immature germinal vesicle positive (GV) and two fully mature, metaphase II arrested (M II) oocytes were obtained from the same patient undergoing IVF treatment. Total RNA was prepared and the polyadenylation status of the Mos mRNA assessed by RNA ligation coupled PCR. The PCR products were excised and subjected to DNA sequence analysis. The size of the PCR products is indicated. This experiment was repeated with similar results using both GV and M II oocytes obtained from three separate patients.

The Endogenous Mos mRNA is Polyadenylated in a Maturation-Dependent Manner in Human Oocytes Given the prevalence of Mos mRNA translational regulation in model organisms and the presence of a consensus CPE sequence in the human Mos 3' UTR, it is desire to determine if the endogenous human Mos mRNA was subject to maturation-dependent polyadenylation as an indicator of mRNA translational activation. To address this issue RNA ligation coupled RT-PCR was employed to assess the polyadenylation status of the Mos mRNA in vivo. This very sensitive technique has been recently employed to assess endogenous maternal mRNA polyadenylation during *Xenopus* oocyte maturation (Charlesworth et al., 2002). Using this assay, an increase in the size of the PCR product is indicative of an increase in the length of the poly[A] tail. Using a forward primer specific to the human Mos mRNA coding region and a primer which is complementary to the DNA oligonucleotide ligated to the end of all the RNAs in the population (P1', see Example 13), a 520 bp PCR product from immature, germinal vesicle positive (GV) human oocytes and a heterogeneous population of PCR products ranging from 580 to 620 bp in mature Metaphase II (MII) human oocytes were observed (FIG. 6, arrowhead and bracket, respectively). The amplified Mos PCR products both from GV and mature MII oocytes were subject to DNA sequencing and confirmed the increased size of PCR product observed in MII oocytes was specifically due to increased length of poly[A] tail. This experiment has been repeated three separate times using oocytes obtained from three independent patients and in each case the GV and MII oocytes were derived from the same donor. The poly[A] tail of the Mos mRNA in immature oocytes was small (around 20 adenylate residues) whereas in the mature, MII oocytes poly[A] tail length is around 60–100 adenylate residues. This increase in Mos mRNA poly[A] tail length is similar to the increase Mos mRNA poly[A] tail length observed during mouse, rat and *Xenopus* oocyte maturation (Sheets, et al., 1994; Goldman, et al. 1988; Lazar, et al., 2002). The results presented herein indicate that the endogenous Mos mRNA undergoes maturation-dependent polyadenylation in human oocytes.

EXAMPLE 16

The Human Mos 3' UTR Interacts with hCPEB1 In Vitro

As described in Example 6, hCPEB1 is expressed in human oocytes where it may regulate the translational activation of maternal mRNAs during human oocyte maturation. To extend these observations it is desired to test if hCPEB1 could interact with the human Mos 3' UTR, since there has been no previous demonstration of a functional CPE in a human 3' UTR. To directly address this issue, GST and chimeric GST-hCPEB1 fusion proteins were prepared by coupled in vitro transcription and translation in rabbit reticulocyte lysates (FIG. 7A) and incubated in vitro with either radiolabelled wild-type or mutant human Mos 3' UTR RNA probes (FIG. 7B) in RNA-EMSA studies.

Figure 7A:
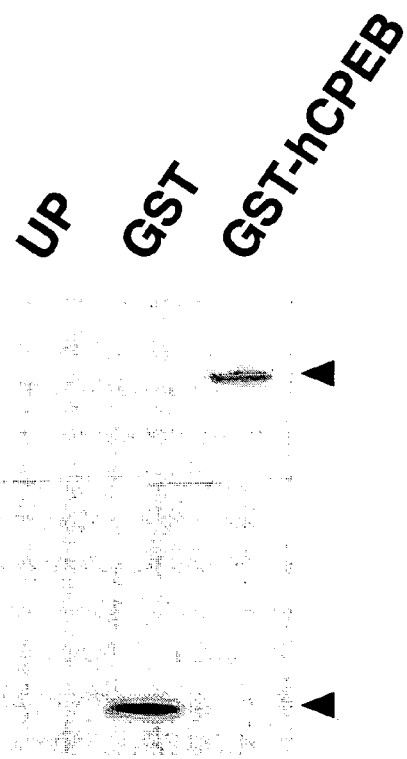
FIGS. 7A–7D shows the human cytoplasmic polyadenylation element binding protein (hCPEB1) specifically interacts with the CPE in the human Mos 3' UTR.
Figure 7B:
Figure 7C:
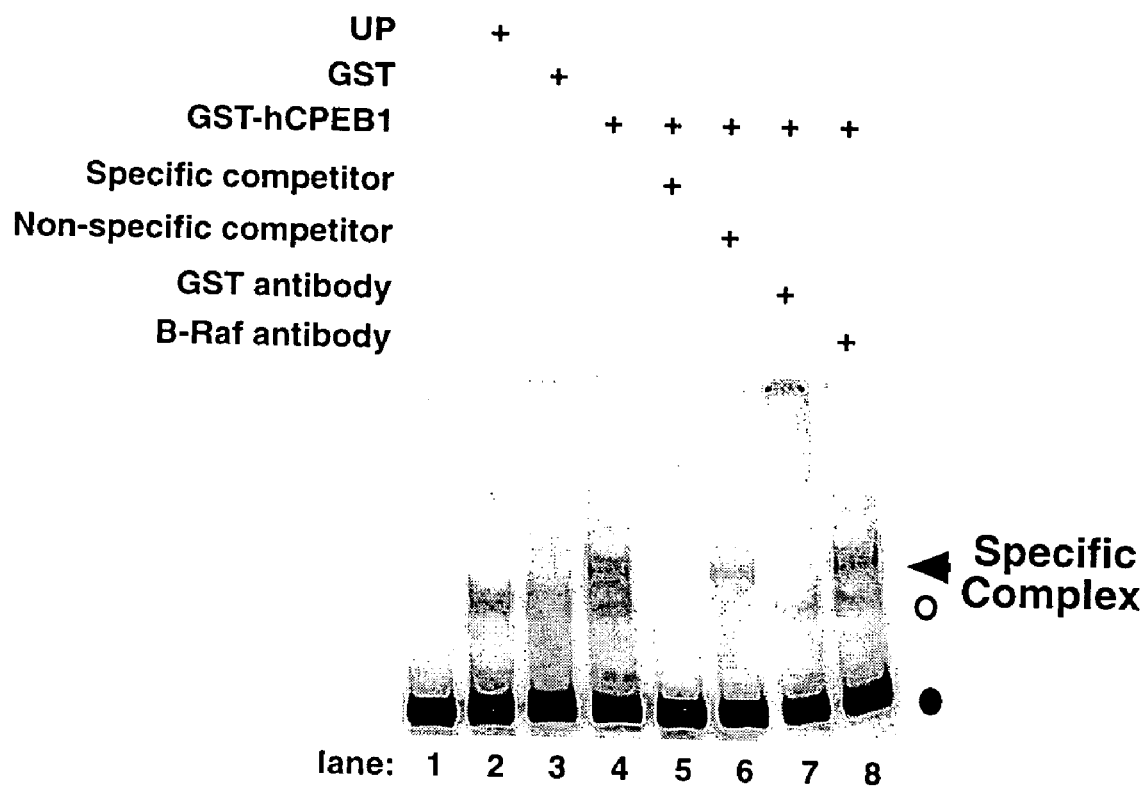

Incubation of the human Mos 3' UTR probe with reticulocyte lysate expressing the GST-hCPEB1 fusion protein resulted in formation of a specific complex (FIG. 7C, arrowhead). To confirm the specificity of hCPEB1 complex formation with the human Mos 3' UTR probe, the complex formation was challenged with 50-fold molar excess of unlabelled RNA probe competitors. Upon addition of unlabelled, wild-type human Mos 3' UTR probe (specific competitor) the formation of the specific complex was abolished (FIG. 7C, lane 5). A non-specific complex was observed with either addition of un-programmed reticulocyte lysate or lysate expressing the GST moiety alone (FIG. 7C, open circle). The formation of non-specific complexes has been previously observed with rabbit reticulocyte lysates in EMSA assays when wild-type or CPE-disrupted *Xenopus* Mos and Wee1 3' UTRs were employed (Charlesworth et al., 2000). Addition of unlabelled, CPE-disrupted mutant 2 human Mos 3'UTR probe (non-specific competitor) had little affect on the formation of the specific complex (FIG. 7C, lane 6), but did eliminate the faster migrating non-specific complex. The specificity of this complex was further verified by challenging with GST antibodies which resulted in a super-shift of the GST-hCPEB1/RNA complex (FIG. 7C, lane 7). The GST antibodies did not affect the formation of the non-specific complex indicating that the GST fusion protein was not involved in this complex. As a control, antibodies to the unrelated B-Raf protein did not affected the formation of the specific complex (FIG. 7C, lane 8). These results indicate that the hCPEB1 protein specifically interacts with the human Mos 3' UTR.

Figure 7D:
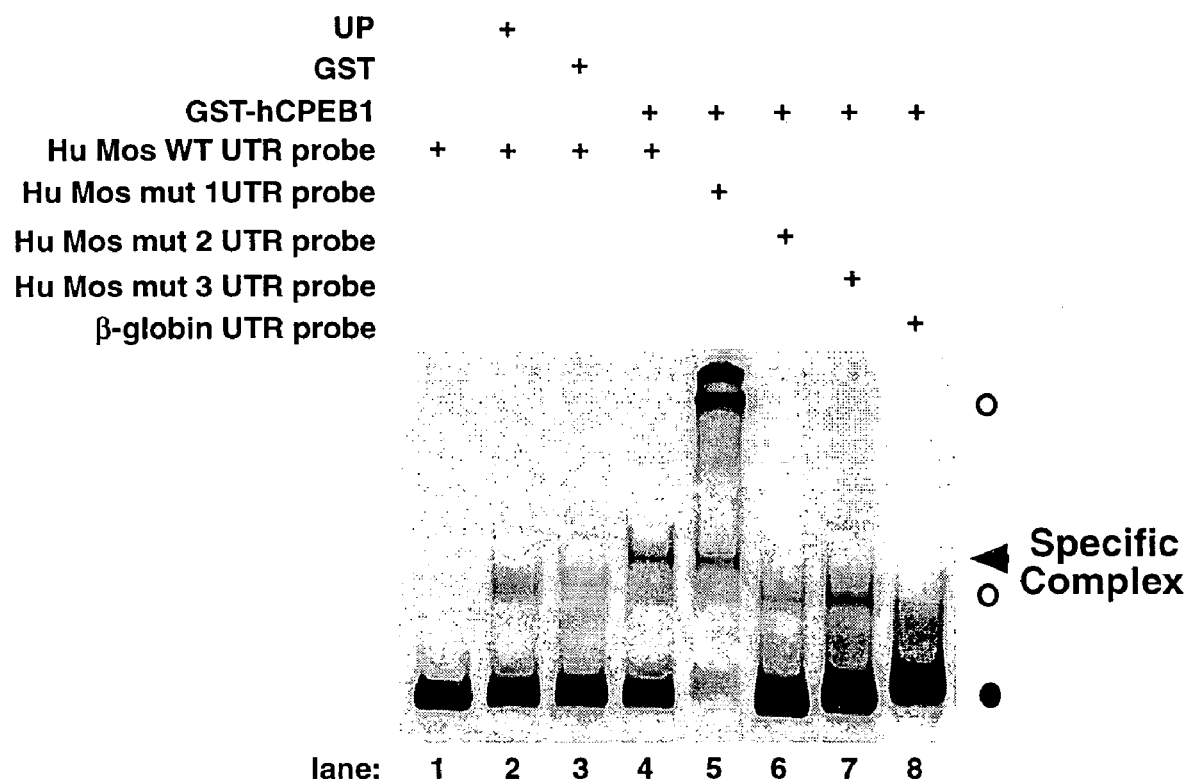

To identify the target of hCPEB1 in the human Mos 3' UTR, a series of EMSA reactions were performed using either wild-type or mutant human Mos 3' UTRs (FIG. 7B). Human Mos UTR mutant 1 encoded a disruption of the $U_4A$ sequence adjacent to the polyadenylation hexanucleotide. Mos UTR mutant 2 encoded a disruption of the 5' $U_5A$ sequence. Human Mos UTR mutant 3 encoded disruptions of both the $U_5A$ and $U_4A$ sequences. As shown in FIG. 7D, a specific complex formation with hCPEB1 was only observed when wild-type or Mos UTR mutant 1 probes were utilized (FIG. 7D, lanes 4 and 5). No specific complex formation was observed with Mos mutant 2 or 3 UTR probes (FIG. 7D, lanes 6 and 7). These results indicate that hCPEB1 can interact specifically with the $U_5A$ CPE in the human Mos 3' UTR. As additional controls, no specific complex formation was observed with a b-globin 3' UTR probe (which lacks CPE sequences) (FIG. 7D lane 8) or when unprogrammed or GST moiety alone lysates were used (FIG. 7D, lanes 2 and 3 respectively).

EXAMPLE 17

The Human Mos 3' UTR Exerts Translational Regulation in a Model System

Figure 8A:
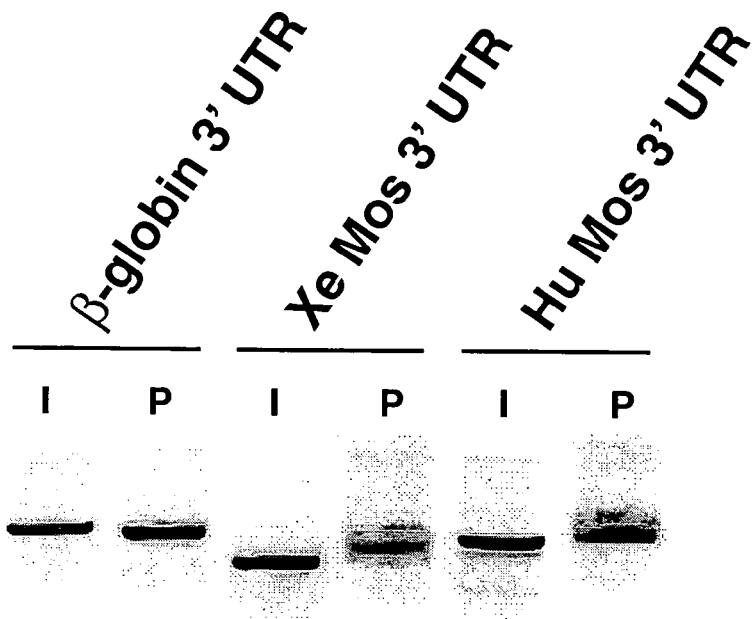
FIGS. 8A–8B shows the human Mos 3' UTR directs cytoplasmic polyadenylation in *Xenopus* oocytes. *Xenopus* immature oocytes were injected with a GST reporter mRNA coupled to the indicated 3' UTRs. Oocytes were then either left untreated (I) or stimulated with progesterone (P) for 16 hours. Pooled oocyte samples were prepared from each condition and both total RNA and protein lysate prepared from each pooled sample.

The next step is to determine if the $U_5A$ CPE sequence in the Mos 3' UTR could direct translational regulation. Prior studies have shown that the heterologous Xenopus oocyte and embryo systems are extremely useful to examine evolutionarily conserved mRNA translational regulatory elements (Knaut, et al., 2002; Gebauer and Richter, 1996; Verrotti, et al., 1996; Thompson, et al., 2000). To this end the human Mos 3' UTR downstream of a GST reporter RNA was fused and the chimeric RNA was injected into immature Xenopus oocytes. As controls for this experiment, immature Xenopus oocytes were separately injected with GST reporter RNAs fused to either the Xenopus b-globin 3' UTR or the Xenopus Mos 3' UTR. The b-globin 3' UTR lacks CPEs sequences and is not subject to regulated mRNA translational activation (Charlesworth et al., 2000) while the Xenopus Mos 3' UTR contains both PRE and CPE sequences and directs translational repression in immature oocytes and translational induction in progesterone stimulated, maturing oocytes (Charlesworth et al., 2002; Sheets et al., 1994; Stebbins-Boaz et al., 1996). The injected oocytes were then split into two pools and either left untreated (immature) or stimulated with progesterone to induce oocyte maturation. Total RNA and protein lysates were prepared from the same pooled oocyte samples after 16 hours of culture and polyadenylation of the reporter RNA assessed by RNA ligation coupled PCR. Reporter RNA translation was assessed by western blot for GST protein accumulation. As expected, the GST reporter RNA fused to the b-globin 3' UTR was not polyadenylated in progesterone-stimulated oocytes, and in fact underwent deadenylation (FIG. 8A). By contrast, the human Mos 3' UTR behaved similarly to the Xenopus Mos 3' UTR and directed polyadenylation in response to progesterone stimulation. DNA sequence analysis confirmed that the increased size of the PCR products in progesterone-stimulated oocytes was due to an increased size of the poly[A] tail.

Figure 8B:
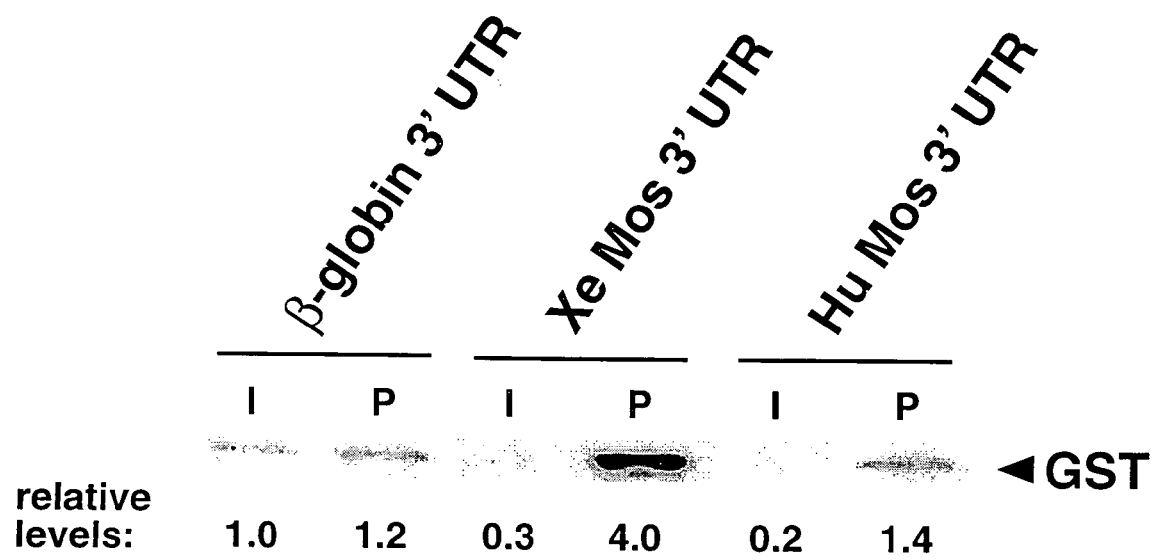

Analysis of the protein lysates from the same pooled oocyte samples analyzed for polyadenylation in FIG. 8A, revealed that GST protein accumulation under the control of the b-globin 3' UTR was similar in immature and progesterone-stimulated oocytes as expected, whereas the human Mos 3' UTR exerted translational regulation of GST protein accumulation (FIG. 8B). The human Mos 3' UTR, like the Xenopus Mos 3' UTR, directed translational repression in immature oocytes (where the level of GST accumulation was less than that observed with the b-globin 3' UTR) and this repression was relieved in progesterone stimulated oocytes.

EXAMPLE 18

The Human Mos has One Functional CPE Sequence

Figure 9A:
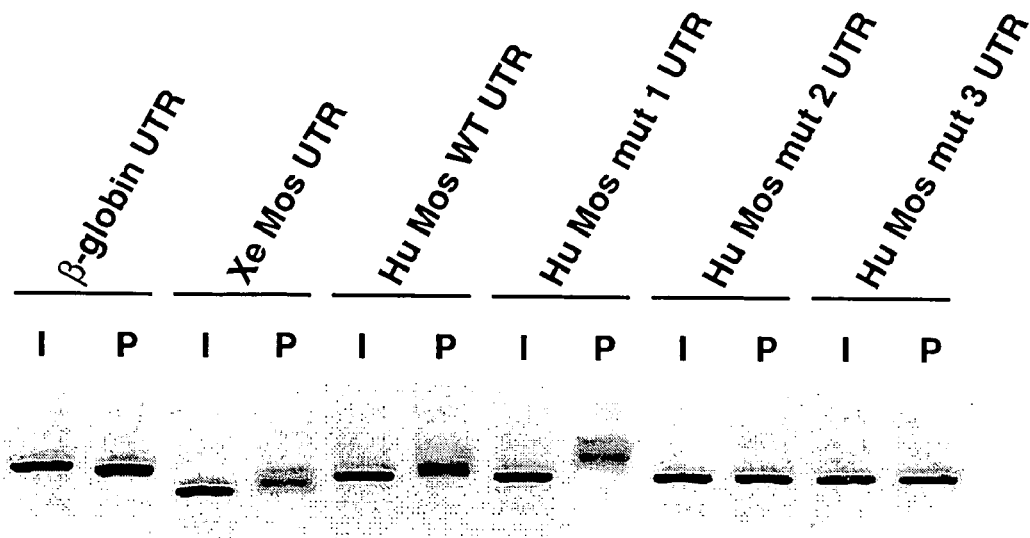
FIG. 9 shows the human Mos 3' UTR contains one functional CPE. Immature *Xenopus* oocytes from the same frog were injected with GST reporter RNA coupled to the indicated 3' UTR. The injected oocytes were then split into two pools and either left untreated (I) or stimulated with progesterone (P). Pooled oocyte samples were prepared as described in FIG. 4 and analyzed for cytoplasmic polyadenylation by RNA ligation coupled PCR as shown in FIG. 9A or for GST protein accumulation by western blotting as shown in FIG. 9B. In response to progesterone stimulation, an average of 35 adenylate residues were added to the *Xenopus* Mos 3' UTR, 30 adenylate residues to the wild-type human Mos 3' UTR and 77 adenylate residues to the human Mos mutant 1 UTR. GST protein levels were quantitated and the relative levels are indicated (normalized to the levels controlled by the human Mos mutant 2 UTR). While the experiment was repeated four times with similar results, the slight increase in GST accumulation directed by the human Mos mutant 3 UTR was not consistently observed.

The wild-type and mutant human Mos 3' UTRs shown in FIG. 7A were then utilized to determine if the cytoplasmic polyadenylation and translational control exerted by the human Mos 3' UTR was regulated by the $U_5A$ CPE. Chimeric GST reporter RNAs fused to the wild-type or mutant human Mos 3' UTRs were injected into immature Xenopus oocytes. As can be seen in FIG. 9A, the length of the wild-type and mutant Mos 3' UTRs were indistinguishable in immature oocytes (FIG. 9A). Following progesterone stimulation, only the reporter mRNAs retaining the $U_5A$ CPE (wild-type and mutant 1 human Mos UTRs) were able to direct maturation-dependent polyadenylation. Disruption of the $U_5A$ CPE sequence (mutant 2) completely ablated progesterone-stimulated cytoplasmic polyadenylation of the GST reporter RNA. Similarly, the double mutant UTR (mutant 3) did not direct progesterone-stimulated polyadenylation. These results indicate that the $U_5A$ sequence is a bona fide CPE. Curiously, the length of poly[A] tail was significantly longer in the absence of the polyadenylation hexanucleotide adjacent $U_4A$ sequence (mutant 1).

Figure 9B:
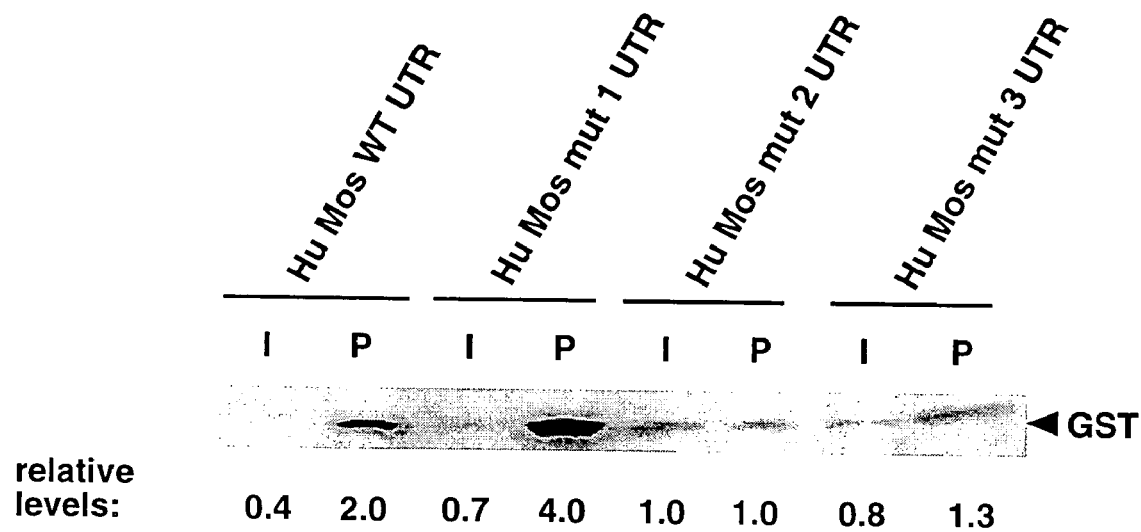

Consistent with the polyadenylation data observed in FIG. 9A, translational regulation of the GST reporter RNA also required the 5' $U_5A$ CPE sequence. Both the $U_5A$ CPE-containing reporter mRNAs (wild-type and mutant 1 Mos UTR) repressed GST accumulation in immature oocytes and this repression was relieved in progesterone-stimulated oocytes (FIG. 9B). By contrast, the mutant 2 and mutant 3 UTR reporter chimeras which lack the $U_5A$ CPE had lost their ability to exert translational regulation as evidenced by similar levels of GST protein accumulation in immature and progesterone-stimulated oocytes. The mutant 1 Mos UTR consistently directed accumulation of GST to levels that exceed the levels controlled by the wild-type human Mos 3' UTR. The results presented herein indicate that the $U_5A$ CPE sequence is necessary for the translational regulation exerted by the wild-type human Mos 3' UTR. Moreover, CPE-directed polyadenylation correlates with the relief of repression and translational induction in mature oocytes.

EXAMPLE 19

Figure 10:
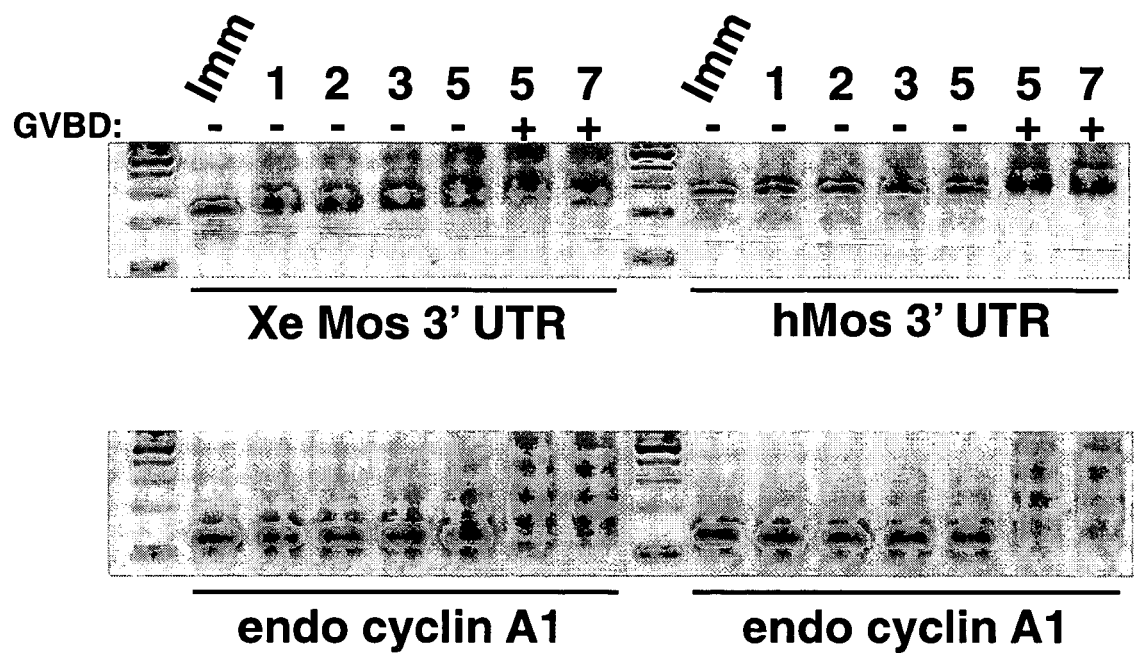
FIG. 10 shows differential temporal regulation of *Xenopus* and human Mos 3' UTR-directed polyadenylation in maturing oocytes. Immature *Xenopus* oocytes were injected with GST reporter RNA coupled to either the *Xenopus* (Panel A, XeMos) or human (Panel B, hMos) 3' UTRs. For each GST reporter RNA, the injected oocytes were then split into two pools and either left untreated (Imm) or stimulated with progesterone for the indicated times. Pooled oocyte samples were prepared as described in FIG. 4 and analyzed for cytoplasmic polyadenylation by RNA ligation coupled PCR using a GST forward primer common to both injected RNA constructs. For each experimental time point, endogenous cyclin A1 mRNA polyadenylation was also assessed. At the 5 hour time point, 50% of the oocyte population had reached GVBD and the oocytes were pooled based on whether they had (+) or had not (−) completed GVBD. All the injected oocytes had matured by 7 hours.

Differential Temporal Polyadenylation of the Human and Xenopus Mos 3' UTRs in Maturing Oocytes It is recently reported that the Xenopus Mos mRNA is polyadenylated and translationally activated temporally early during progesterone-stimulated oocyte maturation (Charlesworth et al., 2002; Charlesworth et al., 2004). This early polyadenylation significantly precedes GVBD and is regulated by a PRE sequence, in a CPE-independent manner. In contrast to PRE-directed polyadenylation, CPE-directed polyadenylation was shown to occur temporally later during maturation around the time of GVBD (Charlesworth et al., 2002; Charlesworth et al., 2004). The available evidence suggests that the CPE sequence in the Xenopus Mos 3' UTR acts subsequent to the PRE and functions to maintain the extended poly[A] tail after GVBD. No consensus PRE sequence (VBTYHWWHYNWDHWHRTHHDKBTW (SEQ ID NO. 20), see (Charlesworth et al., 2004)) is present in the human Mos 3' UTR sequence suggesting that the temporal control of Mos mRNA translational induction may be fundamentally different between these two species. To directly assess any possible temporal differences in the ability of the Xenopus and human Mos 3' UTRs to induce cytoplasmic polyadenylation, GST reporter RNAs were injected into immature oocytes and the time course of induced polyadenylation in response to progesterone stimulation was analyzed (FIG. 10), rather than simply analyze the fully mature oocytes samples as shown in FIG. 9A. Consistent with earlier studies, the PRE-dependent early polyadenylation of the Xenopus Mos 3' UTR begins prior to GVBD (FIG. 10, upper left panel, 1 hour after progesterone stimulation). The length of the *Xenopus* Mos 3' UTR continued to increase up until the oocytes completed GVBD. In the same RNA sample preparations, the endogenous CPE-dependent *Xenopus* cyclin A1 mRNA was polyadenylated later in maturation at a time when the oocytes have reached GVBD (FIG. 10, lower left panel). In contrast to the *Xenopus* Mos 3' UTR, polyadenylation regulated by the human Mos 3' UTR occurs later in maturation when the oocytes had completed GVBD in a profile similar to the endogenous *Xenopus* cyclin A1 mRNA analyzed from the same sample preparations (FIG. 10, right panels). Taken together with the data shown in FIG. 9, these findings indicate that the human Mos 3' UTR lacks an early acting PRE sequence and exerts temporally late cytoplasmic polyadenylation via a single CPE sequence in the 3' UTR.

A primary finding of this study is that the human Mos mRNA undergoes cytoplasmic polyadenylation in human oocytes in a maturation-dependent manner. This finding supports a model in which human oocyte maturation is regulated by the CPE-dependent polyadenylation and translational activation of the maternal Mos mRNA. Consistent with this interpretation, it has been shown that inhibition of protein synthesis with cyclohexamide or microinjection of Mos antisense oligonucleotides perturb human oocyte maturation (Hashiba et al., 2001; Pal et al., 1994). Furthermore, analyses of the 3' UTR database (Pesole et al., 2000) indicate that at least 11% of human 3' UTRs have a $U_5A_{1-2}U$ CPE consensus sequence and imply that CPE-dependent translational control of other human maternal mRNAs encoding cell cycle regulatory proteins may also contribute to oocyte maturation. The findings presented herein suggest that regulated maternal mRNA translational induction is a universal mechanism for controlling vertebrate oocyte maturation. The intriguing differences between human and model organisms in CPE-directed translational control and the implications for human fertility are discussed below.

Using the heterologous *Xenopus* oocyte system, it is demonstrated herein that the human Mos 3' UTR has a single functional CPE of sequence $U_5A$. This CPE directs translational repression of a reporter RNA in immature oocytes and this repression is relieved as the oocytes re-enter the meiotic cell cycle and progress through maturation. The relief of repression correlates with the maturation-dependent cytoplasmic polyadenylation of the human Mos 3' UTR. It is interesting to note that primate (human and monkey) Mos mRNA 3' UTRs, may only have one functional CPE sequence. Indeed, using the heterologous *Xenopus* oocyte system, mutational disruption of the $U_5A$ CPE sequence completely ablated maturation-dependent polyadenylation of the human Mos 3' UTR (FIG. 9A). In contrast, the murine Mos 3' UTR has two functional CPE sequences, either of which can direct maturation-dependent cytoplasmic polyadenylation (Gebauer et al., 1994). Similarly, rat and pig Mos 3' UTR sequences have been reported (Newman and Dai 1996; van der Hoorn and Firzlaff, 1984) and are predicted to contain two functional $U_5A$ CPEs. The second, polyadenylation nucleotide sequence-adjacent, CPE in rodent and porcine Mos 3' UTRs ($U_5A$) is a $GU_4A$ sequence in primates. The present study shows that the residual $U_4A$ sequence does not function as a CPE in the human Mos 3' UTR: it fails to interact with the human CPEB1 protein (FIG. 7C); it does not direct maturation-dependent polyadenylation in *Xenopus* oocytes (FIG. 9A); and does not mediate translational repression in immature *Xenopus* oocytes (FIG. 9B). Interestingly, the $U_4A$ sequence may influence the translational regulation exerted by the human Mos 3' UTR. Mutational disruption of the $U_4A$ sequence (mutant 1 UTR) resulted in an increased length of poly[A] tail in response to progesterone-stimulation (FIG. 9A) and increased translation of GST above the levels seen with the wild-type human Mos 3' UTR (FIG. 9B). It is thus possible that the $U_4A$ sequence functions in some way to antagonize CPE-directed polyadenylation and temper Mos mRNA translation. Whether the $U_4A$ sequence influences the secondary structure of the Mos 3' UTR or whether it serves as a specific target for a trans acting regulatory protein remains to be determined. Irrespective of mechanism, it is of note that the functionality of a CPE has been previously reported to be context dependent in model organisms, where the presence of other sequences in the 3' UTR can modulate the extent of CPE-directed polyadenylation and translational activation (Ballantyne et al., 1997; Charlesworth et al., 2000; Gebauer et al., 1994; McGrew and Richter 1990; Simon et al. 1992; Stebbins-Boaz and Richter 1994).

Why the human Mos 3' UTR only retains one functional CPE while the rodent Mos 3' UTRs have two CPEs is unclear at this juncture. It is possible that the presence of two CPE sequences in the rodent Mos 3' UTR may facilitate enhanced Mos translation during oocyte maturation when compared to the human Mos 3' UTR. In this regard it is noted herein that progress through meiotic maturation to metaphase II arrest in human oocytes is significantly slower than that in rodent oocytes (Edwards 1980) suggesting that the accumulation of cell cycle regulatory proteins may, in part, be rate limiting for meiotic progression in human oocytes.

The analysis presented herein of the human Mos 3' UTR revealed a surprising difference in the ability to control the timing of mRNA translational activation. Unlike the *Xenopus* Mos 3' UTR which directs PRE-dependent temporally early cytoplasmic polyadenylation and translational activation prior to GVBD (see FIG. 10 and Charlesworth et al., 2002), a reporter RNA under the control of the human Mos 3' UTR directed temporally late, CPE-dependent, polyadenylation in *Xenopus* oocytes which occurred coincident with GVBD (FIG. 10). This finding supports a recent study showing that temporally early, pre-GVBD mRNA cytoplasmic polyadenylation occurs via a CPE-independent mechanism, whereas CPE-dependent polyadenylation occurs temporally late during oocyte maturation (at or after GVBD) irrespective of whether the 3' UTR has one or more CPEs (Charlesworth et al., 2004). In contrast to the *Xenopus* Mos mRNA 3' UTR which contains both a PRE and a CPE, our findings suggest the human Mos 3' UTR lacks a functional PRE and only exerts temporally late CPE-dependent translational control. Consistent with this interpretation, the PRE consensus sequence (Charlesworth et al., 2004) is absent in the available mammalian Mos 3' UTR sequences (human, mouse, rat, monkey and pig). Moreover, polyadenylation and translation of the rodent Mos mRNA occurs coincident with, or after, GVBD (Gebauer et al., 1994; Lazar et al., 2002; Verlhac et al. 1996). These findings strongly suggest that the mammalian Mos mRNA is subject to temporally late translational activation when compared to the *Xenopus* counterpart. These differences in timing of translational induction likely reflect the differential temporal requirements for Mos protein function during oocyte maturation in these species. For example, while earlier studies using standard antisense Mos oligonucleotides suggested an obligate requirement for Mos mRNA translation for *Xenopus* meiotic cell cycle resumption, activation of maturation promoting factor (MPF, cyclin B/cdc2) and GVBD (Sagata et al., 1988; Sheets et al., 1995), use of Mos morpholino oligonucleotides indicate that like higher vertebrates, Mos mRNA translation is dispensable for meiotic resumption, MPF activation and GVBD (Dupre et al., 2002). These latter findings indicate a non-specific inhibitory effect of standard antisense oligonucleotides on MPF activation. However, in addition to a role in the maintenance of fully mature oocytes in meiotic II metaphase arrest, *Xenopus* oocytes also appear to require Mos mRNA translation to mediate Meiosis I to Meiosis II transition (Dupre et al., 2002; Gross et al., 2000). Oocytes derived from Mos knockout mice were able to progress, albeit with reduced efficiency, through meiosis but failed to maintain meiotic metaphase II arrest and underwent parthenogenetic activation with high frequency (Araki et al., 1996; Colledge et al. 1994; Hashimoto et al. 1994). Thus, Mos function in mammals may be dispensable for the temporally early Meiosis I to Meiosis II transition. However, the maintenance of Meiosis II metaphase arrest most likely represents a universal feature of vertebrate Mos function.

As discussed above, the absence of PRE in the available mammalian Mos mRNA 3' UTRs may reflect the dispensable nature of early Mos mRNA translational activation for meiotic cell cycle progression in these species. Consistent with this proposal, the induction of temporally early *Xenopus* Mos mRNA translational activation is mediated by a PRE sequence which is responsive to MAP kinase signaling, independently of MPF activation. Indeed, both Mos mRNA translational induction and MAP kinase activation precede MPF activation in response to progesterone stimulation (Charlesworth et al., 2002; Fisher et al., 1999). Temporally late, CPE-dependent mRNA translational activation in *Xenopus* is MPF responsive (Charlesworth et al., 2002). In contrast to the *Xenopus* situation, MPF activation precedes MAP kinase activation in maturing rat and mouse oocytes, (Lazar et al., 2002; Verlhac et al., 1993; Verlhac et al., 1994; Zernicka-Goetz et al., 1997). Moreover, in the rat, translational induction of the Mos mRNA requires MPF activation (Josefsberg et al., 2003). Since Meiosis I to Meiosis II transition can occur in the absence of Mos function in rodent oocytes (Araki et al., 1996; Colledge et al. 1994; Hashimoto et al. 1994; Hashimoto, 1996; Josefsberg et al., 2003), a temporally early induction of Mos mRNA translation is not essential for mammalian meiotic cell cycle progression. Rather, an MPF-responsive, CPE-dependent Mos mRNA translational induction at or after GVBD may be sufficient for the accumulation of Mos protein necessary for Meiotic metaphase II arrest and prevention of parthenogenetic activation.

While current in vitro fertilization (IVF) regimes employ in vivo matured oocytes or in vitro maturation of aspirated GV positive oocytes, both sources of oocytes have inherent complications. The success of IVF protocols has a significant dependency on the age of the oocyte donor where successful fertility outcomes decrease with age (Krey et al., 2001) and in vitro human oocyte maturation can be accomplished but is associated with a loss of developmental competence, particularly the reduction or absence of specific proteins in oocytes cultured to metaphase II (Trounson et al., 2001; Moor et al., 1998). Oocyte GVBD is a useful morphological marker of meiotic progression but can also be observed in oocytes in advanced stages of follicular atresia. Thus, completion of GVBD does not necessarily indicate oocyte maturity and acquisition of full developmental potential. While GVBD can be readily assessed by light microscopy, there has hitherto been no reliable indicator of cytoplasmic maturation competence. A diagnostic indicator of cytoplasmic competency of oocytes following in vitro maturation would be an invaluable tool to combat both the cost of unsuccessful fertilization procedures and reduce the emotional burden of participating patients. Typical IVF protocols involve the maturation of 4–10 oocytes. While the RNA ligation coupled PCR assay we employ herein is an invasive technique, analysis of endogenous Mos mRNA polyadenylation as an indicator of maternal mRNA translational activation in one or two representative oocytes from a maturation protocol may be useful to indicate cytoplasmic maturation competence and possible success for fertility outcome of the remaining sister oocytes.

In summary, evidence is provided that regulated cytoplasmic polyadenylation occurs in humans and may serve to control human oocyte meiotic maturation as it does in model organisms. In addition to regulating oocyte maturation, we note that CPE-directed mRNA translational control has been recently implicated in learning and memory in both rodent and Aplysia model systems (Liu et al., 2003; Wu et al., 1998; Si et al., 2003; Si et al., 2003). It will be interesting to determine if regulated cytoplasmic polyadenylation also contributes to neuronal function in humans.

The following references were cited herein:
Altschul et al., (1997). Nucleic Acids Res. 25:3389–3402.
Araki, et al., (1996) *Biol Reprod* 55, 1315–1324.
Ballantyne, et al., (1997) *Mol. Biol. Cell* 8, 1633–1648.
Bally-Cuif et al., (1998). Mech. Dev. 77:31–47.
Barkoff et al., (2000). Dev. Biol. 220:97–109.
Braude et al., (1988). Nature 332:459–461.
Charlesworth et al., (2000). Dev. Biol. 227:706–719.
Charlesworth, et al., (2002) *EMBO J.* 21, 2798–2806.
Charlesworth, et al., (2004) J. Biol. Chem., 279, 17650–17659
Colledge, et al., (1994) *Nature* 370, 65–68.
Daar, et al., (1991) *Journal Of Cell Biology* 114, 329–335.
Davidson (1986). Gene activity in early development, 3rd Edition. Academic Press, London.
de Moor, et al., J. D. (1997) *Mol. Cell. Biol.* 17, 6419–6426.
de Moor and Richter, (1999). EMBO J. 18:2294–2303.
Dupre, et al., (2002) *Embo J* 21, 4026–4036.
Edwards, R. G. (1980) *Conception in the human female*, Academic Press, New York.
Ferby, I et al., (1999) *Genes And Development* 13, 2177–2189.
Fisher, et al., (1999) *Development* 126, 4537–4546.
Fox, C et al., (1989) *Genes Dev.* 3, 2151–2162.
Gebauer and Richter, (1996). Proc. Natl. Acad. Sci. 93:14602–14607.
Gebauer, et al., (1994) *EMBO J.* 13, 5712.
Goldman, et al., (1988) *Oncogene* 3, 159–162.
Gray and Wickens, (1998). Annu. Rev. Cell Dev. Biol. 14:399–458.
Gross, et al., (2000) *Curr Biol* 10, 430–438.
Hake and Richter, (1994) Cell 79:617–627.
Hake et al., (1998). Mol. Cell. Biol. 18:685–693.
Hashiba, et al., (2001) *Fertil Steril* 76, 143–147.
Hashimoto, et al., (1994) *Nature* 370, 68–71.
Hashimoto, N. (1996) *Horm Res* 46 Suppl 1, 11–14.
Hochegger, et al., (2001) *Development* 128, 3795–3807.
Howard et al., (1999). Mol. Cell. Biol. 19:1990–1999.
Josefsberg, et al., (2003) *Biol Reprod* 68, 1282–1290.
Knaut, et al., (2002) *Curr Biol* 12, 454–466.
Krey et al., (2001) *Ann NY Acad Sci* 943, 26–33.
Lazar, et al., (2002) *Mol Endocrinol* 16, 331–341.
Liu, J., and Schwartz, J. H. (2003) *Brain Res* 959, 68–76.
MacNicol et al., (1997) Gene 196:25–29.
Machaca, K., and Haun, S. (2002) *J Cell Biol* 156, 75–85.
Mahadevan, et al., (1998) *J Ark Med Soc* 94, 487–489.
McGrew, et al., (1989) *Genes Dev.* 3, 803–815.

McGrew, L. L., and Richter, J. D. (1990) *EMBO J.* 9, 3743–3751.
Melton et al., (1984). Nucleic Acids Res. 12:7035–7056.
Mendez et al., (2000). Nature 404:302–307.
Mendez et al., (2001) *Nat Rev Mol Cell Biol* 2, 521–529.
Minshall et al., (1999). RNA 5:27–38.
Moor, et al., (1998) *Hum Reprod Update* 4, 223–236.
Nakajo, et al., (2000) *Genes Dev.* 14, 328–338.
Newman, B., and Dai, Y. (1996) *Mol Reprod Dev* 44, 275–288.
Pal et al., (1994). Fertil. Steril. 61:496–503.
Paris, J., and Richter, J. D. (1990) *Mol. Cell. Biol.* 10, 5634–5645.
Pesole et al., (2000). Nucleic Acids Res. 28:193–196.
Pesole, et al., (2002) *Nucleic Acids Res* 30, 335–340.
Pool and Martin, (1994) Fertil. Steril. 61:714–719.
Posada, et al., (1993) *Mol Cell Biol* 13, 2546–2553.
Rassa, et al., (2000) *Virology* 274, 438–449.
Rechsteiner and Rogers, (1996). Trends Biochem. Sci. 21:267–271.
Richter, (1999). Microbiol. Mol. Biol. Rev. 63:446–456.
Richter, J. D. (2000) in *Translational Control of Gene Expression* (Sonenberg, et al., eds), pp. 785–805, Cold Spring Harbor Laboratory Press.
Sagata, et al., (1988) *Nature* 335, 519–525.
Sagata, et al., (1989) *Nature* 342, 512–518.
SallEs, et al., (1992) *Genes Dev.* 6, 1202–1212.
Sheets, et al., (1994) *Genes Dev.* 8, 926–938.
Sheets, M. D., Wu, M., and Wickens, M. (1995) *Nature* 374, 511–516.
Shibuya, et al., (1996) *Cell Growth And Differentiation* 7, 235–241.
Simon, et al., (1992) *Genes And Development* 6, 2580–2591.
Si, K., Lindquist, S., and Kandel, E. R. (2003) *Cell* 115, 879–891.
Si, et al., (2003) *Cell* 115, 893–904.
Standart et al., (1993) *Developmental Genetics* 14, 492–499.
Stebbins-Boaz, et al., (1994) *Mol. Cell. Biol.* 14, 5870–5880.
Stebbins-Boaz et al., (1996). EMBO J. 15:2582–2592.
Stebbins-Boaz et al., (1999). Mol. Cell. 4:1017–1027.
Stutz et al., (1998). Genes Dev. 12:2535–2548.
Tay et al., (2000). Dev. Biol. 221:1–9.
Thompson, et al., (2000) *Mol Cell Biol* 20, 2129–2137.
Trounson, et al., (2001) *Reproduction* 121, 51–75.
van der Hoorn, et al., (1984) *Nucleic Acids Res* 12, 2147–2156.
Verlhac, et al., (1993) *Dev Biol* 158, 330–340.
Verlhac, et al., (1994) *Development* 120, 1017–1025.
Verlhac, et al., (1996) *Development* 122, 815–822.
Verrotti, et al., (1996) Proc. Natl. Acad. Sci. 93, 9027–9032.
Walker et al., (1999). RNA 5:14–26.
Watson, et al., (1982) *Proc Natl Acad Sci USA* 79, 4078–4082.
Wickens et al., (1996). Translational Control of Developmental Decisions. In: Hershey, et al. (Eds.), Translational Control. Cold Spring Harbor Laboratory Press, Plainview, N.Y., pp. 411–450.
Wickens, et al., (2000) in *Translational Control of Gene Expression* (Sonenberg, et al., eds), pp. 295–370, Cold Spring Harbor Laboratory Press.
Wu et al., (1998). Neuron 21:1129–1139.
Zemicka-Goetz, et al., (1997) *Eur J Cell Biol* 72, 30–38.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

What is claimed is:

1. An isolated DNA encoding human cytoplasmic polyadenylation element binding protein (hCPEB), said DNA is selected from the group consisting of:
   (a) SEQ ID No 1;
   (b) SEQ ID No. 2; and
   (c) DNA that encodes human cytoplasmic polyadenylation element binding protein but differs from (a) or (b) in codon sequence due to the degeneracy of the genetic code.

2. An isolated DNA complementary to the DNA of claim 1.

3. A vector comprising the DNA molecule of claim 1, wherein said vector is adapted for expression in a cell and has regulatory elements necessary for expression of said DNA molecule in the cell.

4. A host cell comprising the vector of claim 3, wherein said vector expresses a human cytoplasmic polyadenylation element binding protein.

5. The cell of claim 4, wherein said cell is selected from group consisting of bacterial cells, mammalian cells, plant cells and insect cells.

* * * * *

SEQUENCE LISTING

<160> NUMBER OF SEQ ID NOS: 28

<210> SEQ ID NO 1
<211> LENGTH: 2779
<212> TYPE: DNA
<213> ORGANISM: Homo sapiens
<220> FEATURE:
<223> OTHER INFORMATION: cDNA sequence of the long form of cytoplasmic
      polyadenylation element binding protein

<400> SEQUENCE: 1

```
taatgtcaat atgttttctg gcattgctac ttcaacatcg tcttccatgt          50
ctggcactgg tttggagcac tcatctctat cagattgtct tctgctaatt         100
cctctggtat gttaactctt ggatttctcc aaggtccatg tcttggaaat         150
cttcactccc aacctttttt tgtcatatct acagtttctt tcatgatttc         200
ctgtattggc tctgtggtaa atctgtgaag tcatgtacaa catctggaaa         250 cagtttttt aagcaggaat ttattatttt gggcatgatg gctttcatgg         300 attttctgt aacaatgatg gcattgtcac tggaagaaga agcaggaagg         350
ataaaagatt gctgggacaa ccaggaagca cctgctctct ccacgtgtag         400
taatgccaat atctttcgaa ggataaatgc catattggat aattctctgg         450
atttcagtag agtctgcact acacctataa accgaggaat tcatgatcat         500
```

-continued

| | |
|---|---|
| ttgccagact tccaggactc tgaagaaaca gttacaagca ggatgctttt | 550 |
| cccaacctct gcgcaagaat cttcccgtgg cctcccagat gcaaatgact | 600 |
| tgtgccttgg cctgcagtcc ctcagtctga caggctggga ccgaccctgg | 650 |
| agcacccagg actcagattc ctcagcccag agcagcacac actcggtact | 700 |
| gagcatgctc cataacccac tgggaaatgt cctaggaaaa ccccccttga | 750 |
| gcttcctgcc tctggatccc cttgggtctg acttggtgga caagtttcca | 800 |
| gcaccctcag ttagaggatc acgcctggac acccggccca tcctggactc | 850 |
| tcgatctagc agcccctctg actcagacac cagtggcttc agctctggat | 900 |
| cagatcatct ctcagatttg atttcaagcc ttcgcatttc tccacctctg | 950 |
| cccttcctgt ctctgtcagg gggtggtccc agagacccct taaagatggg | 1000 |
| ggtagggtct cggatggacc aagagcaagc tgctcttgct gcagtcactc | 1050 |
| cctcccaac cagtgcttca aagagatggc caggagcttc tgtgtggcca | 1100 |
| tcctgggacc cctcgaagc tcccaaagac cccttcagca tagagagaga | 1150 |
| ggccaggctg caccgacaag ctgcagctgt gaatgaagcc acctgtacct | 1200 |
| ggagtggcca gcttcctccc cggaactata agaaccccat ctactcttgc | 1250 |
| aaggtgtttc taggaggtgt tccttgggat attacagaag ctggattagt | 1300 |
| taacaccttc cgtgtttttg gctctttgag tgtggagtgg cctggtaagg | 1350 |
| atggcaagca tccccggtgt cctcccaaag gtaatatgcc taaagggtat | 1400 |
| gtgtatctgg tcttcgaact agagaagtct gtccgatcct tgcttcaggc | 1450 |
| ttgctctcat gacccgctga gcccagatgg cctgagtgaa tattatttca | 1500 |
| agatgtccag ccgaaggatg cgctgcaagg aggtgcaggt gatcccctgg | 1550 |
| gtattagccg acagtaactt tgtccggagc ccatctcaga ggcttgaccc | 1600 |
| cagcaggacg gtgttttgtcg gtgctctgca tggaatgcta aatgctgagg | 1650 |
| ccctggcagc catcttgaac gacctatttg gtggagtggt gtatgccggg | 1700 |
| attgacacag ataagcacaa gtatcccatt ggttctggtc gtgtgacttt | 1750 |
| caataaccaa cggagttacc tgaaagcagt cagcgctgct tttgtggaga | 1800 |
| tcaaaaccac caagttcaca aagaaggttc agattgaccc ctacctagaa | 1850 |
| gattctctgt gtcatatctg cagttctcag cctggtcctt tcttctgtcg | 1900 |
| agatcaggtc tgcttcaaat acttctgccg gagctgctgg cactggcggc | 1950 |
| acagcatgga gggcctgcgc caccacagcc ccctgatgcg gaaccagaag | 2000 |
| aaccgagatt ccagctagag gagctggcct tgcccagtgg cctgtggcgc | 2050 |
| ccaaagctgg caggtcaggc aagcagcctg caccaccctg ccactggcga | 2100 |
| ccagggagct ggcttcccaa ggacaaggga aaattgtagt caccttttgca | 2150 |
| cttgctgaat ctgtctttgt ttctgcacta attaatgcac attgagtttt | 2200 |
| gtcaggtttt gttttcaggg ggtgtaccaa gggcaaggac cctctggctt | 2250 |
| accctccaag cgactctgta gttttcccag attttagttc ctcattttgc | 2300 |
| agatgaaaag cggggaaaaa aaaaaaaaaa aaaattcctg aaggtattga | 2350 |
| cacggatgcc tacacctagg tttatttatt aaaagcgctt ttttacattc | 2400 |
| cttgcaatac tgatggtgat gatgcgcagg tctcattggt ttcattcttg | 2450 |

-continued

| | |
|---|---|
| cagttgccat acagtgcctt tccatttatt taacccccac ctgaacggca | 2500 |
| taaactgagt gttcagctgg tgttttttac tgtaaacaat aaggagactt | 2550 |
| tgctcttcat ttaaaccaaa atcatatttc atattttacg ctcgagggtt | 2600 |
| tttaccggtt cctttttaca ctccttaaaa cagttttttaa gtcgtttgga | 2650 |
| acaaaatatt ttttctttcc tggcagcttt taacattata gcaaatttgt | 2700 |
| gtctggggga ctgctggtca ctgtttctca cagttgcaaa tcaaggcatt | 2750 |
| tgcaaccaaa aaaaaaaaaa aaaaaaatg | 2779 |

<210> SEQ ID NO 2
<211> LENGTH: 2273
<212> TYPE: DNA
<213> ORGANISM: Homo sapiens
<220> FEATURE:
<223> OTHER INFORMATION: cDNA sequence of the short form of cytoplasmic
      polyadenylation element binding protein

<400> SEQUENCE: 2

| | |
|---|---|
| gacttccagg actctgaaga aacagttaca agcaggatgc ttttcccaac | 50 |
| ctctgcgcaa gaatcttccc gtggcctccc agatgcaaat gacttgtgcc | 100 |
| ttggcctgca gtccctcagt ctgacaggct gggaccgacc ctggagcacc | 150 |
| caggactcag attcctcagc ccagagcagc acacactcgg tactgagcat | 200 |
| gctccataac ccactgggaa atgtcctagg aaaaccccc ttgagcttcc | 250 |
| tgcctctgga tccccttggg tctgacttgg tggacaagtt tccagcaccc | 300 |
| tcagttagag gatcacgcct ggacacccgg cccatcctgg actctcgatc | 350 |
| tagcagcccc tctgactcag acaccagtgg cttcagctct ggatcagatc | 400 |
| atctctcaga tttgatttca agccttcgca tttctccacc tctgcccttc | 450 |
| ctgtctctgt caggggtgg tcccagagac ccttaaaga tgggggtagg | 500 |
| gtctcggatg gaccaagagc aagctgctct tgctgcagtc actccctccc | 550 |
| caaccagtgc ttcaaagaga tggccaggag cttctgtgtg gccatcctgg | 600 |
| gacctcctcg aagctcccaa agacccttc agcatagaga gagaggccag | 650 |
| gctgcaccga caagctgcag ctgtgaatga agccacctgt acctggagtg | 700 |
| gccagcttcc tccccggaac tataagaacc ccatctactc ttgcaaggtg | 750 |
| tttctaggag gtgttccttg ggatattaca gaagctggat tagttaacac | 800 |
| cttccgtgtt tttggctctt tgagtgtgga gtggcctggt aaggatggca | 850 |
| agcatcccg gtgtcctccc aaaggtaata tgcctaaagg gtatgtgtat | 900 |
| ctggtcttcg aactagagaa gtctgtccga tccttgcttc aggcttgctc | 950 |
| tcatgacccg ctgagcccag atggcctgag tgaatattat ttcaagatgt | 1000 |
| ccagccgaag gatgcgctgc aaggaggtgc aggtgatccc ctgggtatta | 1050 |
| gccgacagta actttgtccg gagcccatct cagaggcttg accccagcag | 1100 |
| gacggtgttt gtcggtgctc tgcatggaat gctaaatgct gaggccctgg | 1150 |
| cagccatctt gaacgaccta tttggtggag tggtgtatgc cgggattgac | 1200 |
| acagataagc acaagtatcc cattggttct ggtcgtgtga ctttcaataa | 1250 |
| ccaacggagt tacctgaaag cagtcagcgc tgcttttgtg gagatcaaaa | 1300 |
| ccaccaagtt cacaaagaag gttcagattg acccctacct agaagattct | 1350 |

-continued

| | |
|---|---|
| ctgtgtcata tctgcagttc tcagcctggt cctttcttct gtcgagatca | 1400 |
| ggtctgcttc aaatacttct gccggagctg ctggcactgg cggcacagca | 1450 |
| tggagggcct gcgccaccac agccccctga tgcggaacca gaagaaccga | 1500 |
| gattccagct agaggagctg gccttgccca gtggcctgtg gcgcccaaag | 1550 |
| ctggcaggtc aggcaagcag cctgcaccac cctgccactg gcgaccaggg | 1600 |
| agctggcttc ccaaggacaa gggaaaattg tagtcacctt tgcacttgct | 1650 |
| gaatctgtct ttgtttctgc actaattaat gcacattgag ttttgtcagg | 1700 |
| ttttgttttc aggggtgta ccaagggcaa ggaccctctg gcttaccctc | 1750 |
| caagcgactc tgtagttttc ccagatttta gttcctcatt ttgcagatga | 1800 |
| aaagcgggga aaaaaaaaaa aaaaaaatt cctgaaggta ttgacacgga | 1850 |
| tgcctacacc taggtttatt tattaaaagc gcttttttac attccttgca | 1900 |
| atactgatgg tgatgatgcg caggtctcat tggtttcatt cttgcagttg | 1950 |
| ccatacagtg cctttccatt tatttaaccc ccacctgaac ggcataaact | 2000 |
| gagtgttcag ctggtgtttt ttactgtaaa caataaggag actttgctct | 2050 |
| tcatttaaac caaatcata tttcatattt tacgctcgag ggttttttacc | 2100 |
| ggttcctttt tacactcctt aaaacagttt ttaagtcgtt tggaacaaaa | 2150 |
| tatttttctt ttcctggcag cttttaacat tatagcaaat ttgtgtctgg | 2200 |
| gggactgctg gtcactgttt ctcacagttg caaatcaagg catttgcaac | 2250 |
| caaaaaaaaa aaaaaaaaaa atg | 2273 |

<210> SEQ ID NO 3
<211> LENGTH: 566
<212> TYPE: PRT
<213> ORGANISM: Homo sapiens
<220> FEATURE:
<221> NAME/KEY: VARSPLIC
<223> OTHER INFORMATION: sequence of the long form of cytoplasmic
      polyadenylation element binding protein

<400> SEQUENCE: 3

```
Met Ala Leu Ser Leu Glu Glu Glu Ala Gly Arg Ile Lys Asp Cys
                 5                  10                  15

Trp Asp Asn Gln Glu Ala Pro Ala Leu Ser Thr Cys Ser Asn Ala
                20                  25                  30

Asn Ile Phe Arg Arg Ile Asn Ala Ile Leu Asp Asn Ser Leu Asp
                35                  40                  45

Phe Ser Arg Val Cys Thr Thr Pro Ile Asn Arg Gly Ile His Asp
                50                  55                  60

His Leu Pro Asp Phe Gln Asp Ser Glu Glu Thr Val Thr Ser Arg
                65                  70                  75

Met Leu Phe Pro Thr Ser Ala Gln Glu Ser Ser Arg Gly Leu Pro
                80                  85                  90

Asp Ala Asn Asp Leu Cys Leu Gly Leu Gln Ser Leu Ser Leu Thr
                95                 100                 105

Gly Trp Asp Arg Pro Trp Ser Thr Gln Asp Ser Asp Ser Ser Ala
               110                 115                 120

Gln Ser Ser Thr His Ser Val Leu Ser Met Leu His Asn Pro Leu
               125                 130                 135

Gly Asn Val Leu Gly Lys Pro Pro Leu Ser Phe Leu Pro Leu Asp
               140                 145                 150
```

-continued

Pro Leu Gly Ser Asp Leu Val Asp Lys Phe Pro Ala Pro Ser Val
                155                 160                 165

Arg Gly Ser Arg Leu Asp Thr Arg Pro Ile Leu Asp Ser Arg Ser
                170                 175                 180

Ser Ser Pro Ser Asp Ser Asp Thr Ser Gly Phe Ser Ser Gly Ser
                185                 190                 195

Asp His Leu Ser Asp Leu Ile Ser Ser Leu Arg Ile Ser Pro Pro
                200                 205                 210

Leu Pro Phe Leu Ser Leu Ser Gly Gly Gly Pro Arg Asp Pro Leu
                215                 220                 225

Lys Met Gly Val Gly Ser Arg Met Asp Gln Glu Gln Ala Ala Leu
                230                 235                 240

Ala Ala Val Thr Pro Ser Pro Thr Ser Ala Ser Lys Arg Trp Pro
                245                 250                 255

Gly Ala Ser Val Trp Pro Ser Trp Asp Leu Leu Glu Ala Pro Lys
                260                 265                 270

Asp Pro Phe Ser Ile Glu Arg Glu Ala Arg Leu His Arg Gln Ala
                275                 280                 285

Ala Ala Val Asn Glu Ala Thr Cys Thr Trp Ser Gly Gln Leu Pro
                290                 295                 300

Pro Arg Asn Tyr Lys Asn Pro Ile Tyr Ser Cys Lys Val Phe Leu
                305                 310                 315

Gly Gly Val Pro Trp Asp Ile Thr Glu Ala Gly Leu Val Asn Thr
                320                 325                 330

Phe Arg Val Phe Gly Ser Leu Ser Val Glu Trp Pro Gly Lys Asp
                335                 340                 345

Gly Lys His Pro Arg Cys Pro Pro Lys Gly Asn Met Pro Lys Gly
                350                 355                 360

Tyr Val Tyr Leu Val Phe Glu Leu Glu Lys Ser Val Arg Ser Leu
                365                 370                 375

Leu Gln Ala Cys Ser His Asp Pro Leu Ser Pro Asp Gly Leu Ser
                380                 385                 390

Glu Tyr Tyr Phe Lys Met Ser Ser Arg Arg Met Arg Cys Lys Glu
                395                 400                 405

Val Gln Val Ile Pro Trp Val Leu Ala Asp Ser Asn Phe Val Arg
                410                 415                 420

Ser Pro Ser Gln Arg Leu Asp Pro Ser Arg Thr Val Phe Val Gly
                425                 430                 435

Ala Leu His Gly Met Leu Asn Ala Glu Ala Leu Ala Ala Ile Leu
                440                 445                 450

Asn Asp Leu Phe Gly Gly Val Val Tyr Ala Gly Ile Asp Thr Asp
                455                 460                 465

Lys His Lys Tyr Pro Ile Gly Ser Gly Arg Val Thr Phe Asn Asn
                470                 475                 480

Gln Arg Ser Tyr Leu Lys Ala Val Ser Ala Ala Phe Val Glu Ile
                485                 490                 495

Lys Thr Thr Lys Phe Thr Lys Lys Val Gln Ile Asp Pro Tyr Leu
                500                 505                 510

Glu Asp Ser Leu Cys His Ile Cys Ser Ser Gln Pro Gly Pro Phe
                515                 520                 525

Phe Cys Arg Asp Gln Val Cys Phe Lys Tyr Phe Cys Arg Ser Cys
                530                 535                 540

```
Trp His Trp Arg His Ser Met Glu Gly Leu Arg His Ser Pro
                545                 550                 555
Leu Met Arg Asn Gln Lys Asn Arg Asp Ser Ser
            560                 565

<210> SEQ ID NO 4
<211> LENGTH: 503
<212> TYPE: PRT
<213> ORGANISM: Homo sapiens
<220> FEATURE:
<221> NAME/KEY: VARSPLIC
<223> OTHER INFORMATION: sequence of the short form of cytoplasmic
      polyadenylation element binding protein

<400> SEQUENCE: 4

Asp Phe Gln Asp Ser Glu Glu Thr Val Thr Ser Arg Met Leu Phe
              5                  10                  15

Pro Thr Ser Ala Gln Glu Ser Ser Arg Gly Leu Pro Asp Ala Asn
             20                  25                  30

Asp Leu Cys Leu Gly Leu Gln Ser Leu Ser Leu Thr Gly Trp Asp
             35                  40                  45

Arg Pro Trp Ser Thr Gln Asp Ser Asp Ser Ser Ala Gln Ser Ser
             50                  55                  60

Thr His Ser Val Leu Ser Met Leu His Asn Pro Leu Gly Asn Val
             65                  70                  75

Leu Gly Lys Pro Pro Leu Ser Phe Leu Pro Leu Asp Pro Leu Gly
             80                  85                  90

Ser Asp Leu Val Asp Lys Phe Pro Ala Pro Ser Val Arg Gly Ser
             95                 100                 105

Arg Leu Asp Thr Arg Pro Ile Leu Asp Ser Arg Ser Ser Ser Pro
            110                 115                 120

Ser Asp Ser Asp Thr Ser Gly Phe Ser Ser Gly Ser Asp His Leu
            125                 130                 135

Ser Asp Leu Ile Ser Ser Leu Arg Ile Ser Pro Pro Leu Pro Phe
            140                 145                 150

Leu Ser Leu Ser Gly Gly Gly Pro Arg Asp Pro Leu Lys Met Gly
            155                 160                 165

Val Gly Ser Arg Met Asp Gln Glu Gln Ala Ala Leu Ala Ala Val
            170                 175                 180

Thr Pro Ser Pro Thr Ser Ala Ser Lys Arg Trp Pro Gly Ala Ser
            185                 190                 195

Val Trp Pro Ser Trp Asp Leu Leu Glu Ala Pro Lys Asp Pro Phe
            200                 205                 210

Ser Ile Glu Arg Glu Ala Arg Leu His Arg Gln Ala Ala Ala Val
            215                 220                 225

Asn Glu Ala Thr Cys Thr Trp Ser Gly Gln Leu Pro Pro Arg Asn
            230                 235                 240

Tyr Lys Asn Pro Ile Tyr Ser Cys Lys Val Phe Leu Gly Gly Val
            245                 250                 255

Pro Trp Asp Ile Thr Glu Ala Gly Leu Val Asn Thr Phe Arg Val
            260                 265                 270

Phe Gly Ser Leu Ser Val Glu Trp Pro Gly Lys Asp Gly Lys His
            275                 280                 285

Pro Arg Cys Pro Pro Lys Gly Asn Met Pro Lys Gly Tyr Val Tyr
            290                 295                 300

Leu Val Phe Glu Leu Glu Lys Ser Val Arg Ser Leu Leu Gln Ala
```

-continued

```
                    305                 310                 315

Cys Ser His Asp Pro Leu Ser Pro Asp Gly Leu Ser Glu Tyr Tyr
            320                 325                 330

Phe Lys Met Ser Ser Arg Arg Met Arg Cys Lys Glu Val Gln Val
            335                 340                 345

Ile Pro Trp Val Leu Ala Asp Ser Asn Phe Val Arg Ser Pro Ser
            350                 355                 360

Gln Arg Leu Asp Pro Ser Arg Thr Val Phe Val Gly Ala Leu His
            365                 370                 375

Gly Met Leu Asn Ala Glu Ala Leu Ala Ala Ile Leu Asn Asp Leu
            380                 385                 390

Phe Gly Gly Val Val Tyr Ala Gly Ile Asp Thr Asp Lys His Lys
            395                 400                 405

Tyr Pro Ile Gly Ser Gly Arg Val Thr Phe Asn Asn Gln Arg Ser
            410                 415                 420

Tyr Leu Lys Ala Val Ser Ala Ala Phe Val Glu Ile Lys Thr Thr
            425                 430                 435

Lys Phe Thr Lys Lys Val Gln Ile Asp Pro Tyr Leu Glu Asp Ser
            440                 445                 450

Leu Cys His Ile Cys Ser Ser Gln Pro Gly Pro Phe Phe Cys Arg
            455                 460                 465

Asp Gln Val Cys Phe Lys Tyr Phe Cys Arg Ser Cys Trp His Trp
            470                 475                 480

Arg His Ser Met Glu Gly Leu Arg His His Ser Pro Leu Met Arg
            485                 490                 495

Asn Gln Lys Asn Arg Asp Ser Ser
            500

<210> SEQ ID NO 5
<211> LENGTH: 21
<212> TYPE: DNA
<213> ORGANISM: Artificial Sequence
<220> FEATURE:
<221> NAME/KEY: primer_bind
<223> OTHER INFORMATION: (+) primer to amplify a 180 bp product for
      RT-PCR analysis of human cytoplasmic polyadenylation element
      binding protein expression in immature human oocytes

<400> SEQUENCE: 5
agatgggggt agggtctcgg a                                              21

<210> SEQ ID NO 6
<211> LENGTH: 21
<212> TYPE: DNA
<213> ORGANISM: Artificial Sequence
<220> FEATURE:
<221> NAME/KEY: primer_bind
<223> OTHER INFORMATION: (-) primer to amplify a 180 bp product for
      RT-PCR analysis of human cytoplasmic polyadenylation element
      binding protein expression in immature human oocytes

<400> SEQUENCE: 6
gcagcttgtc ggtgcagcct g                                              21

<210> SEQ ID NO 7
<211> LENGTH: 20
<212> TYPE: DNA
<213> ORGANISM: Artificial Sequence
<220> FEATURE:
<221> NAME/KEY: primer_bind
<223> OTHER INFORMATION: (-) primer for hCPEBL
```

```
<400> SEQUENCE: 7
gcatcctgct tgtaactgtt                                          20

<210> SEQ ID NO 8
<211> LENGTH: 18
<212> TYPE: DNA
<213> ORGANISM: Artificial Sequence
<220> FEATURE:
<221> NAME/KEY: primer_bind
<223> OTHER INFORMATION: (-) primer for hCPEBS

<400> SEQUENCE: 8
ggactgcagg ccaaggca                                            18

<210> SEQ ID NO 9
<211> LENGTH: 21
<212> TYPE: DNA
<213> ORGANISM: Artificial Sequence
<220> FEATURE:
<221> NAME/KEY: primer_bind
<223> OTHER INFORMATION: (+) primer for hCPEBL

<400> SEQUENCE: 9
ggaagaagaa gcaggaagga t                                        21

<210> SEQ ID NO 10
<211> LENGTH: 28
<212> TYPE: DNA
<213> ORGANISM: Artificial Sequence
<220> FEATURE:
<221> NAME/KEY: primer_bind
<223> OTHER INFORMATION: (+) primer for hCPEBS

<400> SEQUENCE: 10
gcggaattcc agcgggaagc atcagcag                                 28

<210> SEQ ID NO 11
<211> LENGTH: 30
<212> TYPE: DNA
<213> ORGANISM: Artificial Sequence
<220> FEATURE:
<221> NAME/KEY: primer_bind
<223> OTHER INFORMATION: a (+) primer designed to amplify the last 48
      nucleotides of the Mos 3' UTR from pGEM Mos
      321 UTR

<400> SEQUENCE: 11
gcgggatcca ttccatatgt gaatatatag                               30

<210> SEQ ID NO 12
<211> LENGTH: 20
<212> TYPE: DNA
<213> ORGANISM: Artificial Sequence
<220> FEATURE:
<221> NAME/KEY: primer_bind
<223> OTHER INFORMATION: T7 promoter primer

<400> SEQUENCE: 12
taatacgact cactataggg                                          20

<210> SEQ ID NO 13
<211> LENGTH: 36
<212> TYPE: DNA
<213> ORGANISM: Artificial Sequence
<220> FEATURE:
<221> NAME/KEY: primer_bind
```

```
<223> OTHER INFORMATION: (+) PCR primer to construct plasmid
      pGEM XeMos mut UTR

<400> SEQUENCE: 13
cgcggatccc ccgggcacta gtagccagga gttcat                         36

<210> SEQ ID NO 14
<211> LENGTH: 42
<212> TYPE: DNA
<213> ORGANISM: Artificial Sequence
<220> FEATURE:
<221> NAME/KEY: primer_bind
<223> OTHER INFORMATION: (-) PCR primer to construct plasmid
      pGEM XeMos mut UTR

<400> SEQUENCE: 14
cgtctagaca aatcaatttc tttattacca aactatatat tc                  42

<210> SEQ ID NO 15
<211> LENGTH: 25
<212> TYPE: DNA
<213> ORGANISM: Artificial Sequence
<220> FEATURE:
<221> NAME/KEY: primer_bind
<223> OTHER INFORMATION: hCPEB-specific reverse primer

<400> SEQUENCE: 15
ggggatccag aggcaggaag ctcaa                                     25

<210> SEQ ID NO 16
<211> LENGTH: 173
<212> TYPE: DNA
<213> ORGANISM: Homo sapiens
<220> FEATURE:
<221> NAME/KEY: exon
<223> OTHER INFORMATION: first non-coding exon of hCPEBS

<400> SEQUENCE: 16
ggcagcggga agcatcagca gcctgatcac atgctggccc agtctgtaat           50
gcagacggga taggggtgtg tgtgtgaggg gagggggcct gtatggcaac          100
tgctcttgcc ccagcgtccc caaaagtgca gaggcagcgg ctgcagcatc          150
cagccagctt ggatgtctgg cct                                      173

<210> SEQ ID NO 17
<211> LENGTH: 35
<212> TYPE: DNA
<213> ORGANISM: Artificial Sequence
<220> FEATURE:
<223> OTHER INFORMATION: forward primer for human Mos 3' UTR

<400> SEQUENCE: 17
cgcggatcct tagctgaaaa cctggtcaag ataag                          35

<210> SEQ ID NO 18
<211> LENGTH: 35
<212> TYPE: DNA
<213> ORGANISM: Artificial Sequence
<220> FEATURE:
<223> OTHER INFORMATION: reverse primer for human Mos 3' UTR

<400> SEQUENCE: 18
cggtctagat aaaggagttt ttagtaactt tattt                          35

<210> SEQ ID NO 19
```

```
<211> LENGTH: 24
<212> TYPE: DNA
<213> ORGANISM: Homo sapiens
<220> FEATURE:
<223> OTHER INFORMATION: forward primer used with human Mos
      3' UTR primer

<400> SEQUENCE: 19
cggttgctct gagaagttgg aaga                                              24

<210> SEQ ID NO 20
<211> LENGTH: 24
<212> TYPE: DNA
<213> ORGANISM: Xenopus laevis
<220> FEATURE:
<221> NAME/KEY:
<222> LOCATION: 1-2, 4-16, 18-22, 24
<223> OTHER INFORMATION: consensus sequences of PRE; n = any, v = a or
      g or c, b = g or c or t, y = t or c, h = a or c or t, w = a or t,
      d = a or g or t, r = g or a, k = g or t

<400> SEQUENCE: 20
vbtyhwwhyn wdhwhrthhd kbtw                                              24

<210> SEQ ID NO 21
<211> LENGTH: 119
<212> TYPE: DNA
<213> ORGANISM: Homo sapiens
<220> FEATURE:
<223> OTHER INFORMATION: human MOS 3' UTR

<400> SEQUENCE: 21
ctgaaaacct ggtcaagata agttttgtc tgattctatt tctttttaaa                   50
ggaagtggag atgtcgaaga aaacatattt gtaggatgga gttttagaaa                 100
ataaagttac taaaaactc                                                   119

<210> SEQ ID NO 22
<211> LENGTH: 161
<212> TYPE: DNA
<213> ORGANISM: Unknown
<220> FEATURE:
<223> OTHER INFORMATION: monkey MOS 3' UTR

<400> SEQUENCE: 22
ctgaaaactg cgtcaagata agttgttctg attctgtttg tttttaaagg                  50
aagtggagat gtcgaagaaa acatatttgt gggatggagt tttagaaaat                 100
aaagttactt aaaaactcct ttagtctcca atgcttttc taccacacat                  150 agcaaagcac a                                                           161

<210> SEQ ID NO 23
<211> LENGTH: 127
<212> TYPE: DNA
<213> ORGANISM: Unknown
<220> FEATURE:
<223> OTHER INFORMATION: mouse MOS 3' UTR

<400> SEQUENCE: 23
ctccatcgag ccgattgtag agataagctt tgttttttgt ttattttttt                  50
aaagaagtaa ggatggtgtg gagaaaacat accactaggg catatttta                  100 ggaaataaag ttaccacgaa cttcagc                                          127

<210> SEQ ID NO 24
```

```
-continued
<211> LENGTH: 111
<212> TYPE: DNA
<213> ORGANISM: Unknown
<220> FEATURE:
<223> OTHER INFORMATION: rat MOS 3' UTR

<400> SEQUENCE: 24
ctccatcgag ccgatgtgca gataagcttt tcgtttctgt ttatttttaa          50
ataagtaagg atgggctttt agggcatatt tttagaaaat aaagttacta         100
caaacttcac c                                                    111

<210> SEQ ID NO 25
<211> LENGTH: 30
<212> TYPE: DNA
<213> ORGANISM: Homo sapiens
<220> FEATURE:
<223> OTHER INFORMATION: wildtype human Mos

<400> SEQUENCE: 25
tgtttttaaa gagttttaga aaataaagtt                                30

<210> SEQ ID NO 26
<211> LENGTH: 30
<212> TYPE: DNA
<213> ORGANISM: Artificial Sequence
<220> FEATURE:
<223> OTHER INFORMATION: mutant human Mos mut 1

<400> SEQUENCE: 26
tgtttttaaa gagtttggga aaataaagtt                                30

<210> SEQ ID NO 27
<211> LENGTH: 30
<212> TYPE: DNA
<213> ORGANISM: Artificial Sequence
<220> FEATURE:
<223> OTHER INFORMATION: mutant human Mos mut 2

<400> SEQUENCE: 27
tgtttgggaa gagttttaga aaataaagtt                                30

<210> SEQ ID NO 28
<211> LENGTH: 30
<212> TYPE: DNA
<213> ORGANISM: Artificial Sequence
<220> FEATURE:
<223> OTHER INFORMATION: mutant human Mos mut 3

<400> SEQUENCE: 28
tgtttgggaa gagtttggga aaataaagtt                                30
```